(12) United States Patent
Becker

(10) Patent No.: US 8,317,816 B2
(45) Date of Patent: *Nov. 27, 2012

(54) BALLOON CATHETERS AND METHODS FOR TREATING PARANASAL SINUSES

(75) Inventor: Bruce B. Becker, Woodland Hills, CA (US)

(73) Assignee: Acclarent, Inc., Menlo Park, CA (US)

( * ) Notice: Subject to any disclaimer, the term of this patent is extended or adjusted under 35 U.S.C. 154(b) by 1879 days.

This patent is subject to a terminal disclaimer.

(21) Appl. No.: 10/259,300

(22) Filed: Sep. 30, 2002

(65) Prior Publication Data

US 2004/0064150 A1 Apr. 1, 2004

(51) Int. Cl.
*A61M 29/00* (2006.01)
(52) U.S. Cl. .................. 606/196; 606/199
(58) Field of Classification Search .......... 606/192–196, 606/199; 604/96.01; 600/207
See application file for complete search history.

(56) References Cited

U.S. PATENT DOCUMENTS

| | | |
|---|---|---|
| 446,173 A | 2/1891 | Hancock |
| 504,424 A | 9/1893 | De Pezzer |
| 513,667 A | 1/1894 | Buckingham |
| 705,346 A * | 7/1902 | Hamilton ............ 606/192 |
| 798,775 A | 9/1905 | Forsyth |
| 816,792 A | 4/1906 | Green et al. |
| 1,080,934 A | 12/1913 | Shackleford |
| 1,200,267 A | 10/1916 | Sunnergren |
| 1,650,959 A | 11/1927 | Pitman |
| 1,735,519 A | 11/1929 | Vance |
| 1,828,986 A | 10/1931 | Stevens |
| 2,201,749 A | 5/1940 | Vandegrift |
| 2,525,183 A | 3/1947 | Robison |
| 2,493,326 A | 1/1950 | Trinder |
| 2,847,997 A | 8/1958 | Tibone |
| 2,899,227 A | 8/1959 | Gschwend |
| 2,906,179 A | 9/1959 | Bower |

(Continued)

FOREIGN PATENT DOCUMENTS

CH 668188 12/1988

(Continued)

OTHER PUBLICATIONS

Kozlov et al., "Diagnosis and Treatment of Sinusitis by Yamik Sinus Catheters", Rhinology, 1996, 34:123-4.

(Continued)

*Primary Examiner* — Kevin T Truong
*Assistant Examiner* — Sameh Boles
(74) *Attorney, Agent, or Firm* — Steptoe & Johnson LLP

(57) ABSTRACT

A set of sinus balloon catheters are provided for treating a patient's paranasal sinus system, including dilating prepared openings, and natural ostia and ducts and excising sinus cavities. These include a balloon catheter with a bend placing a distal segment at 90° to a proximal segment and a balloon catheter which is substantially straight. The catheters have sufficient stiffness and column strength that the balloon carrying distal segment of the catheter can be pushed into the prepared opening, natural ostium or duct, or sinus to be excised. The catheters have appropriate inflated working diameters and appropriate outer diameters with the balloon deflated that will enable the catheter to be pushed into the respective prepared opening, natural ostium or duct, or sinus cavity to be excised. The methods use the balloon catheters to dilate prepared openings to selected parts of the sinus system, to dilate natural ostia and ducts of the sinus system, and/or to dilate sinus cavities to remove them.

20 Claims, 9 Drawing Sheets

U.S. PATENT DOCUMENTS

| | | | |
|---|---|---|---|
| 2,995,832 A | 8/1961 | Alderson | |
| 3,009,265 A | 11/1961 | Bezark | |
| 3,037,286 A | 6/1962 | Bower | |
| 3,173,418 A | 3/1965 | Baran | |
| 3,347,061 A | 10/1967 | Stuemky | |
| 3,376,659 A | 4/1968 | Asin et al. | |
| 3,384,970 A | 5/1968 | Avalear | |
| 3,393,073 A | 7/1968 | Reutenauer et al. | |
| 3,435,826 A | 4/1969 | Fogarty | |
| 3,469,578 A | 9/1969 | Bierman | |
| 3,481,043 A | 12/1969 | Esch | |
| 3,486,539 A | 12/1969 | Jacuzzi | |
| 3,506,005 A | 4/1970 | Gilio et al. | |
| 3,509,638 A | 5/1970 | Macleod | |
| 3,515,888 A | 6/1970 | Lewis | |
| 3,527,220 A | 9/1970 | Summers | |
| 3,531,868 A | 10/1970 | Stevenson | |
| 3,552,384 A | 1/1971 | Pierie et al. | |
| 3,624,661 A | 11/1971 | Shebanow et al. | |
| 3,731,963 A | 5/1973 | Pond | |
| 3,792,391 A | 2/1974 | Ewing | |
| 3,800,788 A | 4/1974 | White | |
| 3,802,096 A | 4/1974 | Matern | |
| 3,804,081 A | 4/1974 | Kinoshita | |
| 3,834,394 A | 9/1974 | Hunter et al. | |
| 3,850,176 A | 11/1974 | Gottschalk | |
| 3,856,000 A | 12/1974 | Chikama | |
| 3,859,993 A | 1/1975 | Bitner | |
| 3,871,365 A | 3/1975 | Chikama | |
| 3,894,538 A | 7/1975 | Richter | |
| 3,903,893 A | 9/1975 | Scheer | |
| 3,910,617 A | 10/1975 | Scalza et al. | |
| 3,921,636 A | 11/1975 | Zaffaroni | |
| 3,948,254 A | 4/1976 | Zaffaroni | |
| 3,948,262 A | 4/1976 | Zaffaroni | |
| 3,967,618 A | 7/1976 | Zaffaroni | |
| 3,993,069 A | 11/1976 | Buckles et al. | |
| 3,993,072 A | 11/1976 | Zaffaroni | |
| 3,993,073 A | 11/1976 | Zaffaroni | |
| 4,016,251 A | 4/1977 | Higuchi et al. | |
| 4,052,505 A | 10/1977 | Higuchi et al. | |
| 4,053,975 A | 10/1977 | Olbrich et al. | |
| 4,069,307 A | 1/1978 | Higuchi et al. | |
| 4,102,342 A | 7/1978 | Akiyama et al. | |
| 4,138,151 A | 2/1979 | Nakao | |
| 4,184,497 A | 1/1980 | Kolff et al. | |
| 4,198,766 A | 4/1980 | Camin et al. | |
| 4,207,890 A | 6/1980 | Mamajek et al. | |
| 4,209,919 A | 7/1980 | Kirikae et al. | |
| 4,213,095 A | 7/1980 | Falconer | |
| 4,217,898 A | 8/1980 | Theeuwes | |
| 4,268,115 A | 5/1981 | Slemon et al. | |
| 4,299,226 A | 11/1981 | Banka | |
| 4,299,227 A | 11/1981 | Lincoff | |
| 4,338,941 A | 7/1982 | Payton | |
| D269,204 S | 5/1983 | Trepp | |
| 4,388,941 A | 6/1983 | Riedhammer | |
| RE31,351 E | 8/1983 | Falconer | |
| 4,435,716 A | 3/1984 | Zandbergen | |
| 4,437,856 A * | 3/1984 | Valli | 604/29 |
| 4,450,150 A | 5/1984 | Sidman | |
| 4,459,977 A * | 7/1984 | Pizon et al. | 600/17 |
| 4,464,175 A | 8/1984 | Altman et al. | |
| 4,471,779 A | 9/1984 | Antoshkiw et al. | |
| 4,499,899 A | 2/1985 | Lyons, III | |
| 4,554,929 A | 11/1985 | Samson et al. | |
| 4,564,364 A | 1/1986 | Zaffaroni et al. | |
| 4,571,239 A | 2/1986 | Heyman | |
| 4,571,240 A | 2/1986 | Samson et al. | |
| 4,581,017 A | 4/1986 | Sahota | |
| 4,585,000 A | 4/1986 | Hershenson | |
| D283,921 S | 5/1986 | Dyak | |
| 4,589,868 A | 5/1986 | Dretler | |
| 4,596,528 A | 6/1986 | Lewis et al. | |
| D284,892 S | 7/1986 | Glassman | |
| 4,603,564 A | 8/1986 | Kleinhany et al. | |
| 4,606,346 A | 8/1986 | Berg et al. | |
| 4,607,622 A | 8/1986 | Fritch et al. | |
| 4,637,389 A | 1/1987 | Heyden | |
| 4,639,244 A | 1/1987 | Rizk et al. | |
| 4,645,495 A | 2/1987 | Vaillancourt | |
| 4,669,469 A | 6/1987 | Gifford, III | |
| 4,672,961 A | 6/1987 | Davies | |
| 4,675,613 A | 6/1987 | Naegeli et al. | |
| 4,691,948 A | 9/1987 | Austin, Jr. et al. | |
| 4,708,434 A | 11/1987 | Tsuno | |
| 4,708,834 A | 11/1987 | Cohen et al. | |
| 4,726,772 A | 2/1988 | Amplatz | |
| 4,736,970 A | 4/1988 | McGourty et al. | |
| 4,737,141 A | 4/1988 | Spits | |
| 4,748,869 A | 6/1988 | Ohtsuka | |
| 4,748,969 A | 6/1988 | Wardle | |
| 4,748,986 A | 6/1988 | Morrison et al. | |
| 4,755,171 A | 7/1988 | Tennant | |
| 4,771,776 A * | 9/1988 | Powell et al. | 606/194 |
| 4,795,439 A | 1/1989 | Guest | |
| 4,796,629 A * | 1/1989 | Grayzel | 606/194 |
| 4,803,076 A | 2/1989 | Ranade | |
| 4,811,743 A | 3/1989 | Stevens | |
| 4,815,478 A | 3/1989 | Buchbinder et al. | |
| 4,819,619 A | 4/1989 | Augustine et al. | |
| 4,846,186 A | 7/1989 | Box et al. | |
| 4,847,258 A | 7/1989 | Sturm et al. | |
| 4,851,228 A | 7/1989 | Zentner et al. | |
| 4,854,330 A | 8/1989 | Evans, III et al. | |
| 4,862,874 A | 9/1989 | Kellner | |
| 4,867,138 A | 9/1989 | Kubota et al. | |
| 4,883,465 A | 11/1989 | Brennan | |
| 4,897,651 A | 1/1990 | DeMonte | |
| 4,898,577 A | 2/1990 | Badger et al. | |
| 4,917,419 A | 4/1990 | Mora, Jr. et al. | |
| 4,917,667 A | 4/1990 | Jackson | |
| 4,919,112 A | 4/1990 | Siegmund | |
| 4,920,967 A | 5/1990 | Cottonaro et al. | |
| 4,925,445 A | 5/1990 | Sakamoto et al. | |
| 4,940,062 A | 7/1990 | Hampton et al. | |
| 4,943,275 A | 7/1990 | Stricker | |
| 4,946,466 A | 8/1990 | Pinchuk et al. | |
| 4,961,433 A | 10/1990 | Christian | |
| 4,966,163 A | 10/1990 | Kraus et al. | |
| 4,984,581 A | 1/1991 | Stice | |
| 4,994,033 A | 2/1991 | Shockey et al. | |
| 4,998,916 A | 3/1991 | Hammerslag et al. | |
| 4,998,917 A | 3/1991 | Gaiser et al. | |
| 5,001,825 A | 3/1991 | Halpern | |
| 5,002,322 A | 3/1991 | Fukumoto | |
| 5,019,075 A | 5/1991 | Spears et al. | |
| 5,019,372 A | 5/1991 | Folkman et al. | |
| 5,020,514 A | 6/1991 | Heckele | |
| 5,021,043 A | 6/1991 | Becker et al. | |
| 5,024,650 A | 6/1991 | Hagiwara et al. | |
| 5,024,658 A | 6/1991 | Kozlov et al. | |
| 5,026,384 A | 6/1991 | Farr et al. | |
| 5,030,227 A | 7/1991 | Rosenbluth et al. | |
| 5,041,089 A | 8/1991 | Mueller et al. | |
| 5,044,678 A | 9/1991 | Detweiler | |
| 5,053,007 A | 10/1991 | Euteneuer | |
| 5,055,051 A | 10/1991 | Duncan | |
| 5,060,660 A | 10/1991 | Gambale et al. | |
| 5,067,489 A | 11/1991 | Lind | |
| 5,069,226 A | 12/1991 | Yamauchi et al. | |
| 5,087,244 A | 2/1992 | Wolinsky et al. | |
| 5,087,246 A | 2/1992 | Smith | |
| 5,090,595 A | 2/1992 | Vandoninck | |
| 5,090,910 A | 2/1992 | Narlo | |
| 5,112,228 A | 5/1992 | Zouras | |
| 5,116,311 A | 5/1992 | Lofstedt | |
| 5,127,393 A | 7/1992 | McFarlin et al. | |
| 5,137,517 A | 8/1992 | Loney et al. | |
| 5,139,510 A | 8/1992 | Goldsmith, III et al. | |
| 5,139,832 A | 8/1992 | Hayashi et al. | |
| D329,496 S | 9/1992 | Wotton | |
| 5,152,747 A | 10/1992 | Olivier | |
| 5,163,989 A | 11/1992 | Campbell et al. | |
| 5,167,220 A | 12/1992 | Brown | |
| 5,168,864 A | 12/1992 | Shockey | |
| 5,169,043 A | 12/1992 | Catania | |

| | | | |
|---|---|---|---|
| 5,169,386 A * | 12/1992 | Becker et al. ............... 606/192 |
| 5,171,233 A | 12/1992 | Amplatz et al. |
| 5,180,368 A | 1/1993 | Garrison |
| 5,183,470 A | 2/1993 | Wettermann |
| 5,189,110 A | 2/1993 | Ikematu et al. |
| 5,195,168 A | 3/1993 | Yong |
| 5,197,457 A | 3/1993 | Adair |
| 5,207,695 A * | 5/1993 | Trout, III ............... 623/1.36 |
| 5,211,952 A | 5/1993 | Spicer et al. |
| 5,215,105 A | 6/1993 | Kizelshteyn et al. |
| 5,221,260 A * | 6/1993 | Burns et al. ............... 604/99.04 |
| 5,226,302 A | 7/1993 | Anderson |
| 5,230,348 A | 7/1993 | Ishibe et al. |
| 5,236,422 A | 8/1993 | Eplett, Jr. |
| 5,243,996 A | 9/1993 | Hall |
| D340,111 S | 10/1993 | Yoshikawa |
| 5,250,059 A | 10/1993 | Andreas et al. |
| 5,251,092 A | 10/1993 | Brady et al. |
| 5,252,183 A | 10/1993 | Shaban et al. |
| 5,255,679 A | 10/1993 | Imran |
| 5,263,926 A | 11/1993 | Wilk |
| 5,264,260 A | 11/1993 | Saab |
| 5,267,965 A | 12/1993 | Deniega |
| 5,270,086 A * | 12/1993 | Hamlin ............... 428/35.2 |
| 5,273,052 A | 12/1993 | Kraus et al. |
| 5,275,593 A | 1/1994 | Easley et al. |
| 5,286,254 A | 2/1994 | Shapland et al. |
| 5,295,694 A | 3/1994 | Levin |
| 5,300,085 A | 4/1994 | Yock |
| 5,304,123 A | 4/1994 | Atala et al. |
| 5,308,326 A | 5/1994 | Zimmon |
| 5,313,967 A | 5/1994 | Lieber et al. |
| 5,314,417 A | 5/1994 | Stephens et al. |
| 5,315,618 A | 5/1994 | Yoshida |
| 5,333,620 A | 8/1994 | Moutafis et al. |
| 5,334,167 A | 8/1994 | Cocanower |
| 5,336,163 A | 8/1994 | DeMane et al. |
| 5,341,818 A | 8/1994 | Abrams et al. |
| 5,342,296 A | 8/1994 | Persson et al. |
| 5,343,865 A | 9/1994 | Gardineer et al. |
| 5,345,945 A | 9/1994 | Hodgson et al. |
| 5,346,075 A | 9/1994 | Nichols et al. |
| 5,346,508 A | 9/1994 | Hastings |
| 5,348,537 A | 9/1994 | Wiesner et al. |
| 5,350,396 A | 9/1994 | Eliachar |
| 5,356,418 A | 10/1994 | Shturman |
| 5,368,049 A | 11/1994 | Raman et al. |
| 5,368,566 A | 11/1994 | Crocker |
| 5,372,138 A | 12/1994 | Crowley et al. |
| 5,372,584 A | 12/1994 | Zink et al. |
| D355,031 S | 1/1995 | Yoshikawa |
| 5,386,817 A | 2/1995 | Jones |
| 5,391,147 A | 2/1995 | Imran et al. |
| 5,391,179 A | 2/1995 | Mezzoli |
| 5,402,799 A | 4/1995 | Colon et al. |
| 5,409,444 A | 4/1995 | Kensey |
| 5,411,475 A | 5/1995 | Atala et al. |
| 5,411,476 A | 5/1995 | Abrams et al. |
| 5,411,477 A * | 5/1995 | Saab ............... 604/103.13 |
| 5,415,633 A | 5/1995 | Lazarus |
| 5,425,370 A | 6/1995 | Vilkomerson |
| 5,439,446 A | 8/1995 | Barry |
| 5,441,494 A | 8/1995 | Ortiz |
| 5,441,497 A | 8/1995 | Narciso, Jr. |
| 5,450,853 A | 9/1995 | Hastings et al. |
| 5,451,221 A | 9/1995 | Cho et al. |
| 5,454,817 A | 10/1995 | Katz |
| 5,458,572 A | 10/1995 | Campbell et al. |
| 5,465,717 A | 11/1995 | Imran et al. |
| 5,465,733 A | 11/1995 | Hinohara et al. |
| 5,478,565 A | 12/1995 | Geria |
| 5,486,181 A | 1/1996 | Cohen et al. |
| 5,496,338 A | 3/1996 | Miyagi et al. |
| 5,497,783 A | 3/1996 | Urick et al. |
| 5,507,301 A | 4/1996 | Wasicek et al. |
| 5,507,725 A | 4/1996 | Savage et al. |
| 5,507,766 A | 4/1996 | Kugo et al. |
| 5,512,055 A | 4/1996 | Domb et al. |
| 5,514,128 A | 5/1996 | Hillsman et al. |
| 5,519,532 A | 5/1996 | Broome |
| 5,531,676 A | 7/1996 | Edwards et al. |
| 5,533,985 A | 7/1996 | Wong |
| 5,538,008 A | 7/1996 | Crowe |
| 5,546,964 A | 8/1996 | Stangerup |
| 5,549,542 A | 8/1996 | Kovalcheck |
| 5,558,073 A | 9/1996 | Pomeranz et al. |
| 5,558,652 A | 9/1996 | Henke |
| 5,562,619 A | 10/1996 | Mirarchi et al. |
| 5,568,809 A | 10/1996 | Ben-Haim |
| 5,578,007 A | 11/1996 | Imran |
| 5,578,048 A * | 11/1996 | Pasqualucci et al. ......... 606/192 |
| 5,584,827 A | 12/1996 | Korteweg et al. |
| 5,591,194 A | 1/1997 | Berthiaume |
| 5,599,284 A | 2/1997 | Shea |
| 5,599,304 A | 2/1997 | Shaari |
| 5,599,576 A | 2/1997 | Opolski |
| 5,601,087 A | 2/1997 | Gunderson et al. |
| 5,601,594 A | 2/1997 | Best |
| 5,607,386 A | 3/1997 | Flam |
| 5,617,870 A | 4/1997 | Hastings et al. |
| 5,626,374 A | 5/1997 | Kim |
| 5,633,000 A | 5/1997 | Grossman et al. |
| 5,634,908 A | 6/1997 | Loomas |
| 5,638,819 A | 6/1997 | Manwaring et al. |
| 5,643,251 A | 7/1997 | Hillsman et al. |
| 5,645,789 A | 7/1997 | Roucher, Jr. |
| 5,647,361 A | 7/1997 | Damadian |
| 5,656,030 A | 8/1997 | Hunjan et al. |
| 5,662,674 A | 9/1997 | Debbas |
| 5,664,567 A | 9/1997 | Linder |
| 5,664,580 A | 9/1997 | Erickson et al. |
| 5,665,052 A | 9/1997 | Bullard |
| 5,669,388 A | 9/1997 | Vilkomerson |
| 5,673,707 A | 10/1997 | Chandrasekaran |
| 5,676,673 A | 10/1997 | Ferre et al. |
| 5,679,400 A | 10/1997 | Tuch |
| 5,682,199 A | 10/1997 | Lankford |
| 5,685,838 A | 11/1997 | Peters et al. |
| 5,685,847 A | 11/1997 | Barry |
| 5,690,373 A | 11/1997 | Luker |
| 5,693,065 A | 12/1997 | Rains, III |
| 5,694,945 A | 12/1997 | Ben-Haim |
| 5,697,159 A | 12/1997 | Linden |
| 5,700,286 A | 12/1997 | Tartaglia et al. |
| 5,707,389 A | 1/1998 | Louw et al. |
| 5,708,175 A | 1/1998 | Koyanagi et al. |
| 5,711,315 A | 1/1998 | Jerusalmy |
| 5,713,839 A | 2/1998 | Shea |
| 5,713,946 A | 2/1998 | Ben-Haim |
| 5,718,702 A | 2/1998 | Edwards |
| 5,720,300 A | 2/1998 | Fagan et al. |
| 5,722,401 A | 3/1998 | Pietroski et al. |
| 5,722,984 A | 3/1998 | Fischell et al. |
| 5,729,129 A | 3/1998 | Acker |
| 5,730,128 A | 3/1998 | Pomeranz et al. |
| 5,733,248 A | 3/1998 | Adams et al. |
| 5,752,513 A | 5/1998 | Acker et al. |
| 5,762,604 A | 6/1998 | Kieturakis |
| 5,766,158 A | 6/1998 | Opolski |
| 5,775,327 A | 7/1998 | Randolph et al. |
| 5,776,158 A | 7/1998 | Chou |
| 5,779,699 A | 7/1998 | Lipson |
| 5,789,391 A | 8/1998 | Jacobus et al. |
| 5,792,100 A | 8/1998 | Shantha |
| 5,797,878 A | 8/1998 | Bleam |
| 5,803,089 A | 9/1998 | Ferre et al. |
| 5,814,016 A | 9/1998 | Valley et al. |
| 5,819,723 A | 10/1998 | Joseph |
| 5,820,568 A | 10/1998 | Willis |
| 5,824,044 A * | 10/1998 | Quiachon et al. ............ 623/1.23 |
| 5,824,048 A | 10/1998 | Tuch |
| 5,824,173 A | 10/1998 | Fontirroche et al. |
| 5,827,224 A | 10/1998 | Shippert |
| 5,830,188 A | 11/1998 | Abouleish |
| 5,833,608 A | 11/1998 | Acker |
| 5,833,645 A | 11/1998 | Lieber et al. |
| 5,833,650 A | 11/1998 | Imran |
| 5,833,682 A | 11/1998 | Amplatz et al. |

| | | | | | | |
|---|---|---|---|---|---|---|
| 5,836,638 A | 11/1998 | Slocum | | 6,171,303 B1 | 1/2001 | Ben-Haim |
| 5,836,935 A | 11/1998 | Ashton et al. | | 6,174,280 B1 | 1/2001 | Oneda et al. |
| 5,837,313 A | 11/1998 | Ding et al. | | 6,176,829 B1 | 1/2001 | Vilkomerson |
| 5,843,089 A | 12/1998 | Sahatjian et al. | | 6,183,461 B1 | 2/2001 | Matsuura et al. |
| 5,843,113 A | 12/1998 | High | | 6,183,464 B1 | 2/2001 | Sharp et al. |
| 5,846,259 A | 12/1998 | Berthiaume | | 6,190,353 B1 | 2/2001 | Makower et al. |
| 5,857,998 A | 1/1999 | Barry | | 6,190,381 B1 | 2/2001 | Olsen et al. |
| 5,862,693 A | 1/1999 | Myers et al. | | 6,193,650 B1 | 2/2001 | Ryan, Jr. |
| 5,865,767 A | 2/1999 | Frechette et al. | | 6,195,225 B1 | 2/2001 | Komatsu et al. |
| 5,872,879 A | 2/1999 | Hamm | | 6,200,257 B1 | 3/2001 | Winkler |
| 5,873,835 A | 2/1999 | Hastings et al. | | 6,206,870 B1 | 3/2001 | Kanner |
| 5,887,467 A | 3/1999 | Butterweck et al. | | 6,213,975 B1 | 4/2001 | Laksin |
| 5,902,247 A | 5/1999 | Coe et al. | | 6,221,042 B1 | 4/2001 | Adams |
| 5,902,333 A | 5/1999 | Roberts et al. | | 6,231,543 B1 | 5/2001 | Hegde et al. |
| 5,904,701 A | 5/1999 | Daneshvar | | 6,234,958 B1 | 5/2001 | Snoke et al. |
| 5,908,407 A | 6/1999 | Frazee et al. | | 6,238,364 B1 | 5/2001 | Becker |
| 5,916,193 A | 6/1999 | Stevens et al. | | 6,238,391 B1 | 5/2001 | Olsen et al. |
| 5,928,192 A * | 7/1999 | Maahs ............... 604/96.01 | | 6,241,519 B1 | 6/2001 | Sedelmayer |
| 5,931,811 A * | 8/1999 | Haissaguerre et al. .... 604/95.03 | | 6,249,180 B1 | 6/2001 | Maalej et al. |
| 5,931,818 A | 8/1999 | Werp et al. | | 6,254,550 B1 | 7/2001 | McNamara et al. |
| 5,932,035 A | 8/1999 | Koger et al. | | 6,268,574 B1 | 7/2001 | Edens |
| 5,935,061 A | 8/1999 | Acker et al. | | 6,293,957 B1 | 9/2001 | Peters et al. |
| 5,941,816 A | 8/1999 | Barthel et al. | | 6,302,875 B1 | 10/2001 | Makower et al. |
| D413,629 S | 9/1999 | Wolff | | 6,306,105 B1 | 10/2001 | Rooney et al. |
| 5,947,988 A | 9/1999 | Smith | | 6,306,124 B1 | 10/2001 | Jones et al. |
| 5,949,929 A | 9/1999 | Hamm | | D450,382 S | 11/2001 | Nestenborg |
| 5,954,693 A | 9/1999 | Barry | | 6,322,495 B1 | 11/2001 | Snow et al. |
| 5,954,694 A | 9/1999 | Sunseri | | 6,328,564 B1 | 12/2001 | Thurow |
| 5,957,842 A | 9/1999 | Littmann et al. | | 6,332,089 B1 | 12/2001 | Acker et al. |
| 5,968,085 A | 10/1999 | Morris et al. | | 6,332,891 B1 | 12/2001 | Himes |
| 5,971,975 A | 10/1999 | Mills et al. | | 6,340,360 B1 | 1/2002 | Lyles et al. |
| 5,979,290 A | 11/1999 | Simeone | | 6,348,041 B1 | 2/2002 | Klint |
| 5,980,503 A | 11/1999 | Chin | | 6,352,503 B1 | 3/2002 | Matsui et al. |
| 5,980,551 A | 11/1999 | Summers et al. | | 6,375,615 B1 | 4/2002 | Flaherty et al. |
| 5,984,945 A | 11/1999 | Sirhan | | 6,375,629 B1 | 4/2002 | Muni et al. |
| 5,985,307 A | 11/1999 | Hanson et al. | | 6,383,146 B1 | 5/2002 | Klint |
| 5,997,562 A * | 12/1999 | Zadno-Azizi et al. ........ 606/194 | | 6,386,197 B1 | 5/2002 | Miller |
| 6,006,126 A | 12/1999 | Cosman | | 6,389,313 B1 | 5/2002 | Marchitto et al. |
| 6,006,130 A | 12/1999 | Higo et al. | | 6,390,993 B1 | 5/2002 | Cornish et al. |
| 6,007,516 A | 12/1999 | Burbank et al. | | 6,394,093 B1 | 5/2002 | Lethi |
| 6,007,991 A | 12/1999 | Sivaraman et al. | | 6,398,758 B1 | 6/2002 | Jacobsen et al. |
| 6,010,511 A | 1/2000 | Murphy | | 6,409,863 B1 | 6/2002 | Williams et al. |
| 6,013,019 A | 1/2000 | Fischell et al. | | 6,423,012 B1 | 7/2002 | Kato et al. |
| 6,015,414 A | 1/2000 | Werp et al. | | 6,425,877 B1 | 7/2002 | Edwards |
| 6,016,429 A | 1/2000 | Khafizov et al. | | 6,432,986 B2 | 8/2002 | Levin |
| 6,016,439 A | 1/2000 | Acker | | 6,440,061 B1 | 8/2002 | Wenner et al. |
| 6,019,736 A | 2/2000 | Avellanet et al. | | 6,443,947 B1 | 9/2002 | Marko et al. |
| 6,019,777 A | 2/2000 | Mackenzie | | 6,445,939 B1 | 9/2002 | Swanson et al. |
| 6,021,340 A | 2/2000 | Randolph et al. | | 6,450,975 B1 | 9/2002 | Brennan et al. |
| 6,022,313 A | 2/2000 | Ginn et al. | | 6,450,989 B2 | 9/2002 | Dubrul et al. |
| 6,027,461 A | 2/2000 | Walker et al. | | 6,464,650 B2 | 10/2002 | Jafari et al. |
| 6,027,478 A | 2/2000 | Katz | | 6,468,202 B1 | 10/2002 | Irion et al. |
| 6,039,699 A | 3/2000 | Viera | | 6,468,297 B1 | 10/2002 | Williams et al. |
| 6,042,561 A | 3/2000 | Ash et al. | | 6,485,475 B1 | 11/2002 | Chelly |
| 6,048,299 A | 4/2000 | von Hoffmann | | 6,491,940 B1 | 12/2002 | Levin |
| 6,048,358 A | 4/2000 | Barak | | 6,494,894 B2 | 12/2002 | Mirarchi |
| 6,053,172 A | 4/2000 | Hovda et al. | | 6,500,130 B2 | 12/2002 | Kinsella et al. |
| 6,056,702 A | 5/2000 | Lorenzo | | 6,500,189 B1 | 12/2002 | Lang et al. |
| 6,059,752 A | 5/2000 | Segal | | 6,503,087 B1 | 1/2003 | Eggert et al. |
| 6,071,233 A | 6/2000 | Ishikawa et al. | | 6,503,185 B1 | 1/2003 | Waksman et al. |
| 6,079,755 A | 6/2000 | Chang | | 6,511,418 B2 | 1/2003 | Shahidi et al. |
| 6,080,190 A | 6/2000 | Schwartz | | 6,514,249 B1 | 2/2003 | Maguire et al. |
| 6,083,148 A | 7/2000 | Williams | | 6,517,478 B2 | 2/2003 | Khadem |
| 6,083,188 A | 7/2000 | Becker et al. | | 6,524,299 B1 | 2/2003 | Tran et al. |
| 6,086,585 A | 7/2000 | Hovda et al. | | 6,526,302 B2 | 2/2003 | Hassett |
| 6,092,846 A | 7/2000 | Fuss et al. | | 6,527,753 B2 | 3/2003 | Sekine et al. |
| 6,093,150 A | 7/2000 | Chandler et al. | | 6,529,756 B1 | 3/2003 | Phan et al. |
| 6,093,195 A | 7/2000 | Ouchi | | 6,533,754 B1 | 3/2003 | Hisamatsu et al. |
| 6,109,268 A | 8/2000 | Thapliyal et al. | | 6,536,437 B1 | 3/2003 | Dragisic |
| 6,113,567 A | 9/2000 | Becker | | 6,537,294 B1 | 3/2003 | Boyle et al. |
| 6,122,541 A | 9/2000 | Cosman et al. | | 6,543,452 B1 | 4/2003 | Lavigne |
| 6,123,697 A | 9/2000 | Shippert | | 6,544,230 B1 | 4/2003 | Flaherty et al. |
| 6,136,006 A | 10/2000 | Johnson et al. | | 6,549,800 B1 | 4/2003 | Atalar et al. |
| 6,139,510 A | 10/2000 | Palermo | | 6,551,239 B2 | 4/2003 | Renner et al. |
| 6,142,957 A | 11/2000 | Diamond et al. | | 6,569,146 B1 | 5/2003 | Werner et al. |
| 6,148,823 A | 11/2000 | Hastings | | 6,569,147 B1 | 5/2003 | Evans et al. |
| 6,149,213 A | 11/2000 | Sokurenko et al. | | 6,571,131 B1 | 5/2003 | Nguyen |
| 6,159,170 A | 12/2000 | Borodulin et al. | | 6,572,538 B2 | 6/2003 | Takase |
| 6,171,298 B1 | 1/2001 | Matsuura et al. | | 6,572,590 B1 | 6/2003 | Stevens et al. |

| Patent | Date | Inventor |
|---|---|---|
| 6,579,285 B2 | 6/2003 | Sinofsky |
| 6,585,639 B1 | 7/2003 | Kotmel et al. |
| 6,585,717 B1 | 7/2003 | Wittenberger et al. |
| 6,585,794 B2 | 7/2003 | Shimoda et al. |
| 6,596,009 B1 | 7/2003 | Jelic |
| 6,607,546 B1 | 8/2003 | Murken |
| 6,616,601 B2 | 9/2003 | Hayakawa |
| 6,616,659 B1 | 9/2003 | de la Torre et al. |
| 6,616,678 B2 | 9/2003 | Nishtala et al. |
| 6,616,913 B1 | 9/2003 | Mautone |
| 6,619,085 B1 | 9/2003 | Hsieh |
| 6,634,684 B2 | 10/2003 | Spiessl |
| 6,638,233 B2 | 10/2003 | Corvi et al. |
| 6,638,268 B2 | 10/2003 | Niazi |
| 6,638,291 B1 | 10/2003 | Ferrera et al. |
| 6,652,472 B2 | 11/2003 | Jafari et al. |
| 6,652,480 B1 | 11/2003 | Imran et al. |
| 6,663,589 B1 | 12/2003 | Halevy |
| 6,669,689 B2 | 12/2003 | Lehmann et al. |
| 6,669,711 B1 | 12/2003 | Noda |
| 6,672,773 B1 | 1/2004 | Glenn et al. |
| 6,673,025 B1 | 1/2004 | Richardson et al. |
| 6,685,648 B2 | 2/2004 | Flaherty et al. |
| 6,689,096 B1 | 2/2004 | Loubens et al. |
| 6,689,146 B1 | 2/2004 | Himes |
| 6,702,735 B2 | 3/2004 | Kelly |
| 6,712,757 B2 | 3/2004 | Becker et al. |
| 6,714,809 B2 | 3/2004 | Lee et al. |
| 6,716,216 B1 | 4/2004 | Boucher et al. |
| 6,716,813 B2 | 4/2004 | Lim et al. |
| 6,719,749 B1 | 4/2004 | Schweikert et al. |
| 6,755,812 B2 | 6/2004 | Peterson et al. |
| 6,776,772 B1 | 8/2004 | dVrijer et al. |
| 6,780,168 B2 | 8/2004 | Jellie |
| 6,783,522 B2 | 8/2004 | Fischell |
| 6,783,536 B2 | 8/2004 | Vilsmeier et al. |
| 6,786,864 B2 | 9/2004 | Matsuura et al. |
| 6,796,960 B2 | 9/2004 | Cioanta et al. |
| 6,817,976 B2 | 11/2004 | Rovegno |
| 6,832,715 B2 | 12/2004 | Eungard et al. |
| D501,677 S | 2/2005 | Becker |
| 6,851,290 B1 | 2/2005 | Meier et al. |
| 6,860,264 B2 | 3/2005 | Christopher |
| 6,860,849 B2 | 3/2005 | Matsushita et al. |
| 6,878,106 B1 | 4/2005 | Herrmann |
| 6,890,329 B2 | 5/2005 | Carroll et al. |
| 6,899,672 B2 | 5/2005 | Chin et al. |
| 6,902,556 B2 | 6/2005 | Grimes et al. |
| 6,927,478 B2 | 8/2005 | Paek |
| 6,939,361 B1 | 9/2005 | Kleshinski |
| 6,955,657 B1 | 10/2005 | Webler |
| 6,966,906 B2 | 11/2005 | Brown |
| 6,979,290 B2 | 12/2005 | Mourlas et al. |
| 6,991,597 B2 | 1/2006 | Gellman et al. |
| 6,997,931 B2 | 2/2006 | Sauer et al. |
| 6,997,941 B2 | 2/2006 | Sharkey et al. |
| 7,011,654 B2 | 3/2006 | Dubrul et al. |
| 7,022,105 B1 | 4/2006 | Edwards |
| 7,043,961 B2 | 5/2006 | Pandey |
| 7,052,474 B2 | 5/2006 | Castell et al. |
| 7,056,284 B2 | 6/2006 | Martone et al. |
| 7,056,303 B2 | 6/2006 | Dennis et al. |
| 7,074,197 B2 | 7/2006 | Reynolds et al. |
| 7,074,426 B2 | 7/2006 | Kochinke |
| 7,097,612 B2 | 8/2006 | Bertolero et al. |
| 7,108,706 B2 | 9/2006 | Hogle |
| 7,128,718 B2 | 10/2006 | Hojeibane et al. |
| 7,131,969 B1 | 11/2006 | Hovda et al. |
| 7,140,480 B2 | 11/2006 | Drussel et al. |
| D534,216 S | 12/2006 | Makower et al. |
| 7,160,255 B2 | 1/2007 | Saadat |
| 7,169,140 B1 | 1/2007 | Kume |
| 7,169,163 B2 | 1/2007 | Becker |
| 7,172,562 B2 | 2/2007 | McKinley |
| 7,174,774 B2 | 2/2007 | Pawar et al. |
| 7,182,735 B2 | 2/2007 | Shireman et al. |
| 7,184,827 B1 | 2/2007 | Edwards |
| 7,233,820 B2 | 6/2007 | Gilboa |
| 7,235,099 B1 | 6/2007 | Duncavage et al. |
| 7,237,313 B2 | 7/2007 | Skujins et al. |
| 7,252,677 B2 | 8/2007 | Burwell et al. |
| 7,282,057 B2 | 10/2007 | Surti et al. |
| 7,294,345 B2 | 11/2007 | Haapakumpu et al. |
| 7,294,365 B2 | 11/2007 | Hayakawa et al. |
| 7,316,168 B2 | 1/2008 | van der Knokke et al. |
| 7,318,831 B2 | 1/2008 | Alvarez et al. |
| 7,322,934 B2 | 1/2008 | Miyake et al. |
| 7,326,235 B2 | 2/2008 | Edwards |
| 7,338,467 B2 | 3/2008 | Lutter |
| 7,361,168 B2 | 4/2008 | Makower et al. |
| 7,366,562 B2 | 4/2008 | Dukesherer |
| 7,371,210 B2 | 5/2008 | Brock et al. |
| 7,381,205 B2 | 6/2008 | Thommen |
| 7,410,480 B2 | 8/2008 | Muni et al. |
| 7,419,497 B2 | 9/2008 | Muni et al. |
| 7,442,191 B2 | 10/2008 | Hovda et al. |
| 7,452,351 B2 | 11/2008 | Miller et al. |
| 7,454,244 B2 | 11/2008 | Kassab et al. |
| 7,462,175 B2 | 12/2008 | Chang et al. |
| D586,465 S | 2/2009 | Faulkner et al. |
| D586,916 S | 2/2009 | Faulkner et al. |
| 7,488,313 B2 | 2/2009 | Segal et al. |
| 7,493,156 B2 | 2/2009 | Manning et al. |
| 7,500,971 B2 | 3/2009 | Chang et al. |
| D590,502 S | 4/2009 | Geisser et al. |
| 7,520,876 B2 | 4/2009 | Ressemann et al. |
| 7,532,920 B1 | 5/2009 | Ainsworth et al. |
| 7,559,925 B2 | 7/2009 | Goldfarb et al. |
| 7,625,335 B2 | 12/2009 | Deichmann et al. |
| 7,641,668 B2 | 1/2010 | Perry et al. |
| 7,645,272 B2 | 1/2010 | Chang et al. |
| 7,648,367 B1 | 1/2010 | Makower et al. |
| 7,654,997 B2 | 2/2010 | Makower et al. |
| 7,717,933 B2 | 5/2010 | Becker |
| 7,720,521 B2 | 5/2010 | Chang et al. |
| 7,736,301 B1 | 6/2010 | Webler et al. |
| 7,740,642 B2 | 6/2010 | Becker |
| 7,753,929 B2 | 7/2010 | Becker |
| 7,799,048 B2 | 9/2010 | Hudson et al. |
| 7,803,150 B2 | 9/2010 | Chang et al. |
| 7,837,672 B2 | 11/2010 | Intoccia |
| D630,321 S | 1/2011 | Hamilton, Jr. |
| D632,791 S | 2/2011 | Murner |
| 7,988,705 B2 | 8/2011 | Galdonik et al. |
| 2001/0016684 A1 | 8/2001 | Shahidi |
| 2001/0023332 A1 | 9/2001 | Hahnen |
| 2001/0027307 A1 | 10/2001 | Dubrul et al. |
| 2001/0029317 A1 | 10/2001 | Hayakawa |
| 2001/0034530 A1 | 10/2001 | Malackowski et al. |
| 2001/0051761 A1 | 12/2001 | Khadem |
| 2002/0002349 A1 | 1/2002 | Flaherty et al. |
| 2002/0006961 A1 | 1/2002 | Katz et al. |
| 2002/0010384 A1 | 1/2002 | Shahidi et al. |
| 2002/0010426 A1 | 1/2002 | Clayman et al. |
| 2002/0016564 A1 | 2/2002 | Courtney et al. |
| 2002/0026155 A1 | 2/2002 | Mangosong |
| 2002/0029030 A1 | 3/2002 | Lurie et al. |
| 2002/0031941 A1 | 3/2002 | Cote et al. |
| 2002/0055746 A1 | 5/2002 | Burke et al. |
| 2002/0062133 A1 | 5/2002 | Gilson et al. |
| 2002/0077852 A1 | 6/2002 | Ford et al. |
| 2002/0082558 A1 | 6/2002 | Samson et al. |
| 2002/0082583 A1 | 6/2002 | Lerner |
| 2002/0090388 A1 | 7/2002 | Humes et al. |
| 2002/0103459 A1 | 8/2002 | Sparks et al. |
| 2002/0107475 A1 | 8/2002 | Maginot |
| 2002/0116043 A1 | 8/2002 | Garibaldi et al. |
| 2002/0165521 A1 | 11/2002 | Cioanta et al. |
| 2003/0013985 A1 | 1/2003 | Saadat |
| 2003/0014036 A1 | 1/2003 | Varner et al. |
| 2003/0017111 A1 | 1/2003 | Rabito |
| 2003/0032942 A1 | 2/2003 | Theeuwes et al. |
| 2003/0040697 A1 | 2/2003 | Pass et al. |
| 2003/0069521 A1 | 4/2003 | Reynolds et al. |
| 2003/0069549 A1 | 4/2003 | MacMahon et al. |
| 2003/0073955 A1 | 4/2003 | Otawara |
| 2003/0073972 A1 | 4/2003 | Rosenman et al. |
| 2003/0083608 A1 | 5/2003 | Evans et al. |

| | | | | | |
|---|---|---|---|---|---|
| 2003/0083613 A1 | 5/2003 | Schaer | 2006/0173382 A1 | 8/2006 | Schreiner |
| 2003/0100886 A1 | 5/2003 | Segal et al. | 2006/0190022 A1 | 8/2006 | Beyar et al. |
| 2003/0109810 A1 | 6/2003 | Brennan et al. | 2006/0210605 A1 | 9/2006 | Chang et al. |
| 2003/0114732 A1 | 6/2003 | Webler et al. | 2006/0211752 A1 | 9/2006 | Kohn et al. |
| 2003/0120339 A1 | 6/2003 | Banik et al. | 2006/0271024 A1 | 11/2006 | Gertner et al. |
| 2003/0130598 A1 | 7/2003 | Manning et al. | 2007/0005094 A1 | 1/2007 | Eaton et al. |
| 2003/0163154 A1 | 8/2003 | Miyata et al. | 2007/0020196 A1 | 1/2007 | Pipkin et al. |
| 2003/0164952 A1 | 9/2003 | Deichmann et al. | 2007/0049929 A1 | 3/2007 | Catanese et al. |
| 2003/0171650 A1 | 9/2003 | Tartaglia et al. | 2007/0073269 A1 | 3/2007 | Becker |
| 2003/0181827 A1 | 9/2003 | Hojeibane et al. | 2007/0112358 A1 | 5/2007 | Abbott |
| 2003/0185872 A1 | 10/2003 | Kochinke | 2007/0129751 A1 | 6/2007 | Muni et al. |
| 2003/0208194 A1 | 11/2003 | Hovda et al. | 2007/0135789 A1 | 6/2007 | Chang et al. |
| 2003/0209096 A1 | 11/2003 | Pandey et al. | 2007/0167682 A1 | 7/2007 | Goldfarb et al. |
| 2003/0225329 A1 | 12/2003 | Rossner et al. | 2007/0207186 A1 | 9/2007 | Scanlon et al. |
| 2004/0015150 A1 | 1/2004 | Zadno-Azizi | 2007/0208252 A1 | 9/2007 | Makower |
| 2004/0018980 A1 | 1/2004 | Gurney et al. | 2007/0208301 A1 | 9/2007 | Evard et al. |
| 2004/0034311 A1 | 2/2004 | Mihalcik | 2007/0233036 A1 | 10/2007 | Mandpe |
| 2004/0043052 A1 | 3/2004 | Hunter et al. | 2007/0250105 A1 | 10/2007 | Ressemann et al. |
| 2004/0058992 A1 | 3/2004 | Marinello et al. | 2007/0269385 A1 | 11/2007 | Yun et al. |
| 2004/0064083 A1* | 4/2004 | Becker ............ 604/19 | 2007/0293727 A1 | 12/2007 | Goldfarb et al. |
| 2004/0064105 A1 | 4/2004 | Capes et al. | 2007/0293946 A1 | 12/2007 | Gonzales et al. |
| 2004/0064150 A1 | 4/2004 | Becker | 2008/0015540 A1 | 1/2008 | Muni et al. |
| 2004/0097788 A1 | 5/2004 | Mourlas et al. | 2008/0015544 A1 | 1/2008 | Keith et al. |
| 2004/0098017 A1 | 5/2004 | Saab et al. | 2008/0033519 A1 | 2/2008 | Burwell et al. |
| 2004/0116958 A1 | 6/2004 | Gopferich et al. | 2008/0051804 A1 | 2/2008 | Cottler et al. |
| 2004/0122471 A1 | 6/2004 | Toby et al. | 2008/0082045 A1 | 4/2008 | Goldfarb et al. |
| 2004/0127820 A1 | 7/2004 | Clayman et al. | 2008/0097154 A1 | 4/2008 | Makower et al. |
| 2004/0158229 A1 | 8/2004 | Quinn | 2008/0097239 A1 | 4/2008 | Chang et al. |
| 2004/0167440 A1 | 8/2004 | Sharrow | 2008/0097295 A1 | 4/2008 | Makower et al. |
| 2004/0167442 A1 | 8/2004 | Shireman et al. | 2008/0097400 A1 | 4/2008 | Chang et al. |
| 2004/0167443 A1 | 8/2004 | Shireman et al. | 2008/0097514 A1 | 4/2008 | Chang et al. |
| 2004/0181175 A1 | 9/2004 | Clayman et al. | 2008/0097515 A1 | 4/2008 | Chang et al. |
| 2004/0193073 A1 | 9/2004 | DeMello et al. | 2008/0097516 A1 | 4/2008 | Chang et al. |
| 2004/0193139 A1 | 9/2004 | Armstrong et al. | 2008/0103361 A1 | 5/2008 | Makower et al. |
| 2004/0230095 A1 | 11/2004 | Stefanchik et al. | 2008/0103521 A1 | 5/2008 | Makower et al. |
| 2004/0230131 A1 | 11/2004 | Kassab et al. | 2008/0119693 A1 | 5/2008 | Makower et al. |
| 2004/0230156 A1 | 11/2004 | Schreck et al. | 2008/0125046 A1 | 5/2008 | Deng et al. |
| 2004/0236231 A1 | 11/2004 | Knighton et al. | 2008/0125626 A1 | 5/2008 | Chang et al. |
| 2004/0249243 A1 | 12/2004 | Kleiner | 2008/0154250 A1 | 6/2008 | Makower et al. |
| 2004/0249267 A1 | 12/2004 | Gilboa | 2008/0154345 A1 | 6/2008 | Taylor |
| 2004/0254625 A1 | 12/2004 | Stephens et al. | 2008/0187098 A1 | 8/2008 | Gertner et al. |
| 2004/0267347 A1 | 12/2004 | Cervantes | 2008/0188870 A1 | 8/2008 | Andre et al. |
| 2005/0027249 A1 | 2/2005 | Reifart et al. | 2008/0195041 A1 | 8/2008 | Goldfarb et al. |
| 2005/0043706 A1 | 2/2005 | Eaton et al. | 2008/0208242 A1 | 8/2008 | Becker |
| 2005/0049486 A1 | 3/2005 | Urquhart et al. | 2008/0208243 A1 | 8/2008 | Becker |
| 2005/0055077 A1 | 3/2005 | Marco et al. | 2008/0215082 A1 | 9/2008 | Becker |
| 2005/0059931 A1 | 3/2005 | Garrison et al. | 2008/0215083 A1 | 9/2008 | Becker |
| 2005/0089670 A1 | 4/2005 | Large et al. | 2008/0228085 A1 | 9/2008 | Jenkins et al. |
| 2005/0107720 A1 | 5/2005 | Burmeister et al. | 2008/0234720 A1 | 9/2008 | Chang et al. |
| 2005/0107738 A1 | 5/2005 | Slater et al. | 2008/0275483 A1 | 11/2008 | Makower et al. |
| 2005/0113686 A1 | 5/2005 | Peckham | 2008/0281156 A1 | 11/2008 | Makower et al. |
| 2005/0113687 A1 | 5/2005 | Herweck et al. | 2008/0287908 A1 | 11/2008 | Muni et al. |
| 2005/0113850 A1 | 5/2005 | Tagge | 2008/0319424 A1 | 12/2008 | Muni et al. |
| 2005/0119590 A1 | 6/2005 | Burmeister et al. | 2009/0017090 A1 | 1/2009 | Arensdorf et al. |
| 2005/0124856 A1 | 6/2005 | Fujikura et al. | 2009/0028923 A1 | 1/2009 | Muni et al. |
| 2005/0131316 A1 | 6/2005 | Flagle et al. | 2009/0030274 A1 | 1/2009 | Goldfarb et al. |
| 2005/0143687 A1 | 6/2005 | Rosenblatt et al. | 2009/0047326 A1 | 2/2009 | Eaton et al. |
| 2005/0182319 A1 | 8/2005 | Glossop | 2009/0088728 A1 | 4/2009 | Dollar et al. |
| 2005/0228260 A1 | 10/2005 | Burwell et al. | 2009/0093823 A1 | 4/2009 | Chang et al. |
| 2005/0228412 A1 | 10/2005 | Surti | 2009/0156980 A1 | 6/2009 | Eaton et al. |
| 2005/0234507 A1 | 10/2005 | Geske et al. | 2009/0163890 A1 | 6/2009 | Clifford et al. |
| 2005/0240147 A1 | 10/2005 | Makower et al. | 2009/0187089 A1 | 7/2009 | Say et al. |
| 2005/0244472 A1 | 11/2005 | Hughes et al. | 2009/0187098 A1 | 7/2009 | Makower et al. |
| 2005/0245906 A1 | 11/2005 | Makower et al. | 2009/0192492 A1 | 7/2009 | Eaton et al. |
| 2005/0283221 A1 | 12/2005 | Mann et al. | 2009/0198216 A1 | 8/2009 | Muni et al. |
| 2005/0288549 A1 | 12/2005 | Mathis | 2009/0227945 A1 | 9/2009 | Eaton et al. |
| 2005/0288759 A1 | 12/2005 | Jones et al. | 2009/0240112 A1 | 9/2009 | Goldfarb et al. |
| 2006/0004286 A1 | 1/2006 | Chang et al. | 2009/0240237 A1 | 9/2009 | Goldfarb et al. |
| 2006/0004323 A1 | 1/2006 | Chang et al. | 2009/0312745 A1 | 12/2009 | Goldfarb et al. |
| 2006/0063973 A1 | 3/2006 | Makower et al. | 2010/0087811 A1 | 4/2010 | Herrin et al. |
| 2006/0067982 A1 | 3/2006 | Haapakumpu et al. | 2010/0114066 A1 | 5/2010 | Makower et al. |
| 2006/0074318 A1 | 4/2006 | Ahmed et al. | 2010/0121308 A1 | 5/2010 | Muni et al. |
| 2006/0085027 A1 | 4/2006 | Santin et al. | 2010/0174308 A1 | 7/2010 | Chang et al. |
| 2006/0095066 A1 | 5/2006 | Chang et al. | 2010/0174366 A1 | 7/2010 | Avior |
| 2006/0106361 A1 | 5/2006 | Muni et al. | 2010/0198191 A1 | 8/2010 | Clifford et al. |
| 2006/0107957 A1 | 5/2006 | Djupesland | 2010/0198302 A1 | 8/2010 | Shalev |
| 2006/0116749 A1 | 6/2006 | Willink et al. | 2011/0166190 A1 | 7/2011 | Anderson et al. |
| 2006/0149310 A1 | 7/2006 | Becker | | | |
| 2006/0173291 A1 | 8/2006 | Glossop | | | |

FOREIGN PATENT DOCUMENTS

| | | |
|---|---|---|
| CN | 2151720 | 1/1994 |
| CN | 2352818 | 12/1999 |
| DE | 03202878 | 8/1983 |
| DE | 04032096 | 4/1992 |
| DE | 04406077 | 9/1994 |
| DE | 08810044 | 11/1998 |
| DE | 29923582 | 12/2000 |
| DE | 10104663 | 8/2002 |
| DE | 10105592 | 8/2002 |
| EP | 0129634 | 1/1985 |
| EP | 0257605 | 3/1988 |
| EP | 0355996 | 2/1990 |
| EP | 0418391 | 3/1991 |
| EP | 0427852 | 5/1991 |
| EP | 0623582 | 11/1994 |
| EP | 0624349 | 11/1994 |
| EP | 0744400 | 11/1996 |
| EP | 0585757 | 6/1997 |
| EP | 0893426 | 1/1999 |
| EP | 1042998 | 10/2000 |
| EP | 1166710 | 1/2002 |
| EP | 1413258 | 4/2004 |
| EP | 1944053 | 7/2008 |
| FR | 2859377 | 3/2005 |
| FR | 2916144 | 11/2008 |
| GB | 2125874 | 3/1984 |
| GB | 2305174 | 4/1997 |
| JP | 53-067935 | 6/1978 |
| JP | 10-24098 | 1/1989 |
| JP | 3-503011 | 7/1991 |
| JP | 3-504935 | 10/1991 |
| JP | 4-221313 | 8/1992 |
| JP | 5-211985 | 8/1993 |
| JP | 6-277296 | 10/1994 |
| JP | 7-327916 | 12/1995 |
| JP | 8-317989 | 12/1996 |
| JP | 11-507251 | 6/1999 |
| JP | 2000-501634 | 2/2000 |
| JP | 2001-501846 | 2/2001 |
| JP | 2001-095815 | 4/2001 |
| JP | 2001-526077 | 12/2001 |
| JP | 2002-028166 | 1/2002 |
| JP | 2002-508214 | 3/2002 |
| JP | 2002-537908 | 11/2002 |
| JP | 2002-538850 | 11/2002 |
| JP | 2003-062080 | 3/2003 |
| JP | 2003-521327 | 7/2003 |
| JP | 2004-357728 | 12/2004 |
| JP | 2005-532869 | 11/2005 |
| RU | 2213530 | 10/2003 |
| SU | 1662571 | 7/1991 |
| WO | 90/11053 | 10/1990 |
| WO | 90/14865 | 12/1990 |
| WO | 91/17787 | 11/1991 |
| WO | 92/15286 | 9/1992 |
| WO | 92/22350 | 12/1992 |
| WO | 94/12095 | 6/1994 |
| WO | 96/29071 | 9/1996 |
| WO | 97/24161 | 6/1997 |
| WO | 99/24106 | 5/1999 |
| WO | 99/30655 | 6/1999 |
| WO | 99/32041 | 7/1999 |
| WO | 00/09192 | 2/2000 |
| WO | 00/23009 | 4/2000 |
| WO | 00/51672 | 9/2000 |
| WO | 00/53252 | 9/2000 |
| WO | 01/45572 | 6/2001 |
| WO | 01/54558 | 8/2001 |
| WO | 01/56481 | 8/2001 |
| WO | 01/70325 | 9/2001 |
| WO | 01/74266 | 10/2001 |
| WO | 01/97895 | 12/2001 |
| WO | 02/062269 | 8/2002 |
| WO | 03/049603 | 6/2003 |
| WO | 03/063703 | 8/2003 |
| WO | 03/105657 | 12/2003 |
| WO | 2004/006788 | 1/2004 |
| WO | 2004/018980 | 3/2004 |
| WO | 2004/026391 | 4/2004 |
| WO | 2004/082525 A2 | 9/2004 |
| WO | 2004/082525 A3 | 9/2004 |
| WO | 2005/018730 | 3/2005 |
| WO | 2005/077450 | 8/2005 |
| WO | 2005/089670 | 9/2005 |
| WO | 2005/117755 | 12/2005 |
| WO | 2006/034008 | 3/2006 |
| WO | 2006/078884 | 7/2006 |
| WO | 2006/107957 | 10/2006 |
| WO | 2006/116597 | 11/2006 |
| WO | 2006/118737 | 11/2006 |
| WO | 2006/135853 | 12/2006 |
| WO | 2007/111636 | 10/2007 |
| WO | 2007/124260 | 11/2007 |
| WO | 2008/036149 | 3/2008 |
| WO | 2008/045242 | 4/2008 |
| WO | 2008/051918 | 5/2008 |
| WO | 2008/134382 | 11/2008 |

OTHER PUBLICATIONS

Maran et al, "The Use of the Foley Catheter in the Tripod Fracture", J. Laryngol. Otol. 1971, 897-902.
Bartal, J.Laryngol. Otol. 1988, 102:146-7.
Cox et al., Laryngoscope 1986, 96:579.
Daduola, J. Laryngol. Otol, 1989, 4:375-8.
Gadot et al, Int. J. Pediatr. Otorhinolarygol, 1991, 21:97-101.
Podoshin et al, J. Laryngol. Otol. 1967;81:1157-61.
Göttmann, et al.; Balloon Dilatation of Recurrent Ostial Occlusion of the frontal sinus; Abstract No. B-0453, European Congress of Radiology, Mar. 2001.
Göttmann, et al.; Balloon dilatation of recurrent ostial occlusion of the frontal sinus; ECR, Mar. 2, 2001.
Göttmann, et al.; Successfull Treatment of Recurrent Post-operative Frontal Sinus Stenoses by Balloon Dilitation; CIRSE, Oct. 5, 2002.
Göttmann, et al.; Balloon dilatation in the nasal cavity and paranasal sinuses; CIRSE, Sep. 25, 2004.
Robison, J. Mathews, M.D.; Pressure Treatment of Purulent Maxillary Sinusitis, Texas State Journal of Medicine, May 1951, pp. 281-288.
Robison, J. Mathews, M.D.; Pressure Treatment of Maxillary Sinusitis, J.A.M.A., May 31, 1952, pp. 436-440.
Strohm et al.; Le Traitement Des Sténoses Des Voies Aériennes Supérieures Par Dilatation Au Ballon, Sep. 25, 1999.
Ijaduola, T.G.A, "Use of a Foley Catheter for Short-Term Drainage in Frontal Sinus Surgery", The Journal of Laryngology and Otology Apr. 1989, vol. 103, pp. 375-378.
Robison, J. Mathews, "Pressure Treatment of Maxillary Sinusitis", J.A.M.A. May 31, 1952.
Robison, J. Mathews, "Pressure Treatment of Maxillary Sinusitis", Texas State Journal of Medicine, May 1951, pp. 281-288.
Strohm, et al., "Treatment of Stenoses of the Upper Airways by Balloon Dilation", 83rd Annual Conference of the Union of Southwest German Ear, Nose and Throat Specialists, Sep. 25, 1999.
Argon Medical. Maxxim Medical. Ad for Sniper EliteTM Hydrophilic Ni-Ti Alloy Guidewire (2001).
Aust, R., et al 'The Functional Size of the Human Maxillary Ostium in Vivo' Acta. Otolaryn. (1978) vol. 78 pp. 432-435.
Baim, D.S., MD Grossman's Cardiac Catheterization, Angiography, and Intervention (2000) Lippincott Williams & Wilkins pp. 76, 84 & 214.
Barrett, S. 'Be Wary of Neurocranial Restructuring (NCR)' Chirobase (available at: http://www.chirobase.org/06DD/ncr.html) (Jul. 2003.).
Bartal, N. 'An Improved Stent for Use in the Surgical Management of Congenital Posterior Choanal Atresia' J. Laryngol. Otol. (1988) vol. 102 pp. 146-147.
Becker, A.E. 'Restenosis After Angioplasty' The Lancet (1988) vol. 331, No. 8584 p. 532.
Benninger et al. Adult Chronic Rhinosinusitis: Definitions, Diagnosis, Epidemiology, and Pathophysiology Arch Otolaryol Head and Neck Surg. (Sep. 2003) vol. 129 pp. S1-S32.
Bent et al. 'The Frontal Cell as a Cause of Frontal Sinus Obstruction' American Journal of Rhinology. (1994) vol. 8, No. 4 pp. 185.

Binner et al. 'Fibre-Optic Transillumination of the Sinuses: A Comparison of the Value of Radiography and Transillumination in Antral Disease' Clinical Otolaryngology. (1978) vol. 3 pp. 1-11.

Brown, C.L. et al 'Safety and Feasibility of Balloon Catheter Dilation of Paranasal Sinus Ostia: A Preliminary Investigation' Annals of Otology, Rhinology & Laryngology (2006) vol. 115, No. 4 pp. 293-299.

Bumm, P., H. Kaiser et al 'Cortizontherapie, Corticoide in Klinik and Praxis' Thieme, Stuggart (1992) pp. 390-401 [Summary of textbook].

Casiano et al. 'Endoscopic Lothrop Procedure: The University of Miami Experience' American Journal of Rhinology (1998) vol. 12, No. 5 pp. 335-339.

Casserly, I.P. et al Chapter 7. 'Guides and Wires in Percutaneous Coronary Intervention' Strategic Approaches in Coronary Intervention (2006) Lippincott Williams & Wilkins pp. 91-99.

Chien, Y.W. et al. Nasal Systemic Drug Delivery, Drugs and the Pharmaceutical Sciences (1989) Marcel Dekker, Inc. Chapter 3, pp. 39-88.

Cohen et al 'Endoscopic Sinus Surgery: Where we are and where we're going' Current Opinion in Otolaryngology & Head and Neck Surgery (2005) vol. 13 pp. 32-38.

Colla, A. et al 'Trihaloacetylated Enol Ethers—General Synthetic Procedure and Heterocyclic Ring Closure Reactions with Hydroxylamine' Synthesis. (Jun. 1991) pp. 483-486.

Costa, M.N. et al 'Endoscopic Study of the Intranasal Ostium in External Dacryocystorhinostomy Postoperative Influence of Saline Solution and 5-Flurorouracil' Clinics. (2007) vol. 62, Issue 1 pp. 41-46. http://www.scielo.br/scielo.php?pid=S1807-59322007000100007&script=sci_arttext.

Cussler, E.L. *Diffusion: Mass Transfer in Fluid Systems* Cambridge University Press (1996) [Summary of textbook].

Davis, G.E. et al., 'A Complication From Neurocranial Restructuring' Arch Otolaryngology Head Neck Surg. (Apr. 2003) vol. 129 pp. 472-474.

Deutschmann, R. et al. 'A Contribution to the Topical Treatment of [Maxillary] Sinusitis Preliminary Communication' Stomat DDR 26, (1976) pp. 585-592.

Domb, A. et al *Handbook of Biodegradable Polymers* Harwood Academic Publishers (1997) [Summary of textbook].

Draf, W. 'Endonasal Micro-Endoscopic Frontal Sinus Surgery: the Fulda Concept' Op Tech Otolaryngol Head Neck Surg. (1991) vol. 2 pp. 234-240.

Edmond et al 'ENT Surgical Stimulator' Nov. 1998 Final Report Cooperative Agreement No. DAMD17-95-2-5023.

Eremychev, V.A. 'Needles for Puncture and Drainage of the Maxillary Sinus' Meditsinskaya Tekhnika, No. 5 (1974) pp. 54-55.

Feldman, R.L. et al 'New Steerable, Ultra-Low-Profile, Fixed Wire Angioplasty Catheter: Initial Experience With the Cordis Orion™ Steerable PTCA Balloon Catheter' Cathet. Cardiovasc. Diagn. (1990) vol. 19, No. 2 pp. 142-145.

Ford, C.N. 'A Multipurpose Laryngeal Injector Device' Otolaryngol. Head Neck Surg. (1990) vol. 103, No. 1 pp. 135-137.

Friedman, M. M.D., et al 'Frontal Sinus Surgery: Endoscopic Technique' Operative Techniques in Otolarynology—Head and Neck Surgery. (Jun. 2001) vol. 12, No. 2 pp. 60-65.

Friedman, et al 'Intraoperative and Postoperative Assessment of Frontal Sinus Patency by Transillumination' Laryngoscope. (Apr. 2000) vol. 110 pp. 683-684.

Friedman et al 'Middle Turbinate Medialization and Preservation in Endoscopic Surgery' Otolaryngol. Head Neck Surg. (2000) vol. 123, No. 1, Part 1. pp. 76-80.

Fung, M.K.T. 'How I Do It—Head and Neck and Plasic Surgery. A Targeted Problem and its Solution. Template for Frontal Osteoplastic Flap' Laryngoscope. (1986) vol. 96 pp. 578-579.

Gatot, A. et al., 'Early Treatment of Orbital Floor Fractures with Catheter Balloon in Children' Int. J. Pediatric Otorhinolaryngol (1991) vol. 21 pp. 97-101.

Gerus, I.I. et al 'β-Ethoxyvinyl Polyfluroroalkyl Ketones-Versatile Synthones in Fluoroorganic Chemistry' Journal of Fluorine Chemistry. (1994) vol. 69 pp. 195-198. Elsevier Science S.A.

Good, R.H. 'An Intranasal Method for Opening the Frontal Sinus Establishing the Largest Possible Drainage' Laryngoscope. (1908) vol. 18 pp. 266-274.

Gopferich 'Polymer Degradation and Erosion: Mechanisms and Applications' Eur. J. Pharm. Biophar. (1996) vol. 42 pp. 1-11.

Gorlov, D.V. et al 'Acylation of 2-Methoxypropene with Anhydrides and Halides of Perflurocarboxylic Acids in the Presence of Tertiary Amines' Russian Chemical Bulletin. (Sep. 1999) vol. 48 No. 9 pp. 1791-1792. Kluwer Academic/Plenum Publishers.

Gottman, et al. 'Balloon Dilatation in the Nasal Cavity and Paranasal Sinuses' CIRSE. (Sep. 25, 2004) pp. 1-27.

Gottman, et al. 'Balloon Dilatation of Recurrent Ostial Occlusion of the Front Sinus' Abstract No. B-04353. European Congress of Radiology. (Mar. 2, 2001).

Gottman, et al. 'Successful Treatment of Recurrent Post-Operative Frontal Sinus Stenoses by Balloon Dilatation' CIRSE. (Oct. 5, 2002).

Gupta, D. et al 'Dacryocystitis Secondary to an Iatrogenic Foreign Body in the Lacrimal Apparatus' Ear, Nose & Throat Journal (2009) http://findarticles.com/p/articles/mi_m0BUM/is_7_88/ai_n32428620/.

Hashim, et al 'Balloon Compression of the Intermaxillary Sinus for Intractable Post Traumatic Bleeding from the Maxillary Artery' Scandinavian Journal of Plastic and Reconstructive Surgery and Hand Surgery (1999) vol. 33 pp. 321-324.

Hojo, M. et al 'Electrophilic Substitutions of Olefinic Hydrogens II. Acylation of Vinyl Ethers and N Vinyl Amides' Chemistry Letters (1976) pp. 499-502.

Hopf, J.U.G. et al 'Miniature Endoscopes in Otorhinolaryngologic Applications' Min Invas Ther & Allied Technol. (1998) vol. 7, No. 3 pp. 209-218.

Hosemann, W. et al *A Dissection Course on Endoscopic Endonasal Sinus Surgery* (2005) Endo-Press, Tuttlingen pp. 4-37.

Hosemann, W. et al 'Endonasal Frontal Sinusotomy in Surgical Management of Chronic Sinusitis: A Critical Evaluation' American Journal of Rhinology (1997) vol. 11, No. 1 pp. 1-9.

Hosemann, M.E. et al 'Experimentelle Untersuchungen zur Wundheilung in den Nasennebenholhlen. II. Spontaner Wundschluss and medikamentose Effekte im standardisierten Wundmodell.' HNO 39 (1991) pp. 48-54.

Hosemann W.G. et al *Minimally Invasive Endonasal Sinus Surgery* Thieme, Stuttgart, New York (2000) [Summary of textbook].

Hosemann, M.E. et al 'Normal Wound Healing of the Paranasal Sinuses—Clinical and Experimental Investigations' Eur Arch Otorhinolarygol. (1991) vol. 248 pp. 390-394.

Hosemann, W. et al 'Weiterbehandlung nach Nasennebenhohleneingriffen, Part 2: Theapeutische Malβnahmen' HNO akutell 7 (1999) pp. 291-302.

Hospital Corpsman Sickcall Screener's Handbook. Naval Hospital Great Lakes (Apr. 1999) http://www.brooksidepress.org/Products/Operationa.Medicine/DATA. 2001 pp. 1-6.

Hybels, R.L. 'Transillumination During Osteoplastic Frontal Sinusotomy' The Laryngoscope (Sep. 1981) vol. 91 pp. 1560.

Ijaduola, T.G.A. 'Use of a Foley Catheter for Short-Term Drainage in Frontal Sinus Surgery' The Journal of Laryngology and Otology. (1989) vol. 103 pp. 375-378.

Ingals, F. 'New Operation and Instruments for Draining the Frontal Sinus' Ann. Otol Rhinol Laryngol. (1905) vol. 14 pp. 515-519.

Iro, H. et al 'A New Device for Frontal Sinus Endoscopy: First Clinical Report' Otolaryngol. Head Neck Surg. (2001) vol. 125 No. 6 pp. 613-616.

Jacobs, J.B. '100 Years of Frontal Sinus Surgery' Laryngoscope. (1997) vol. 107 pp. 1-36.

Kennedy, D.W., M.D. et al *Diseases of the Sinuses Diagnosis and Management* (Copyright 2001) by B.C. Decker Inc.

Khomutov, S.M. et al 'Dissolution of a Mixture of Steroids in Cyclodextrin Solutions: a Model Description' Pharmaceutical Chemistry Journal. (Nov. 2001) vol. 35, No. 11 pp. 627-629.

Kingdom, T.T. et al 'Image-Guided Surgery of the Sinuses: Current Technology and Applications' Otolaryngol. Clin. North Am. (Apr. 2004) vol. 37, No. 2 pp. 381-400.

Klossek, J.M. et al 'Local Safety of Intranasal Triamcinolone Acetonide: Clinical and Histological Aspects of Nasal Mucosa in the Long-Term Treatment of Perennial Allergic Rhinitis' Rhinology (2001) vol. 39, No. 1 pp. 17-22.

Kozlov et al 'Diagnosis and Treatment of Sinusitis by YAMIK Sinus Catheters' Rhinology (1996) vol. 34. pp. 123-124.

Kuhn, et al. 'The Agger Nasi Cell in Frontal Recess Obstruction: An Anatomic, Radiology and Clinical Correlation' Operative Techniques in Otolaryngology—Head and Neck Surgery (1991) vol. 2, No. 4 pp. 226-231.

Laliberte F. et al 'Clinical and Pathologic Methods to Assess the Long-Term Safety or Nasal Corticosteroids' Allergy (2000) vol. 55, No. 8 pp. 718-722.

Lang, E.V. et al 'Access Systems for Puncture at an Acute Angle' J. Vasc. Interv. Radiol. (1995) vol. 6, No. 5 pp. 711-713.

Lanza, D.C. 'Postoperative Care and Avoiding Frontal Recess Stenosis' International Advanced Sinus Symposium. General Session Abstracts. (1993) Jul. 21-24.

Large, G.C. 'Crystalline Tetracycline Hydrochloride in the Treatment of Acute and Chronic Maxillary Sinusitis' Canad. M. A. J. (1958) vol. 79 pp. 15-16.

Lund, V.J. 'Maximal Medical Therapy for Chronic Rhinosinusitis' Otolaryngol Clin N Am. (2005) vol. 38 pp. 1301-1310.

Maran, A.G.D. et al 'The Use of the Foley Catheter in the Tripod Fracture' J. Laryngol. Otol (1971) vol. 85, Issue 9 pp. 897-902.

May, M. et al 'Frontal Sinus Surgery: Endonasal Drainage Instead of an External Osteopolstic Approach' Op Tech Otolaryngo Head Neck Surgery (1995) vol. 6, No. 3 pp. 184-192.

Medtronic, xomed.com-MicroFrance Catalog Browser. http://www.xomcat.com/xomfrance/index.php?zone=both&cat=18&sub=58&prodline=1272 (Dec. 31, 2003) pp. 1-2.

Mehan, V.K. et al 'Coronary Angioplasty through 4 French Diagnostic Catheters' Cathet. Cardiovasc. Diagn. (1993) vol. 30, No. 1 pp. 22-26.

Mellor, J.M. et al 'Synthesis of Trifluromethylnaphthalenes' Tetrahedron (2000) vol. 56 pp. 10067-10074. Elseview Science Ltd.

Metson, R. et al 'Endoscopic Treatment of Sphenoid Sinusitis' Otolaryngol. Head Neck Surg. (1996) vol. 114, No. 6 pp. 736-744.

Metson, R. 'Holmium: YAG Laser Endoscopic Sinus Surgery: A Randomized Controlled Study' Laryngoscope (Jan. 1996) vol. 106, Issue 1, Supplement 77 pp. 1-18.

Miller et al. 'Management of Fractures of the Supraorbital Rim' Journal of Trauma (Jul. 1978) vol. 18, No. 7 pp. 507-512.

Min, Y-G et al. 'Mucociliary Activity and Histopathology of Sinus Mucosa in Experimental Maxilary Sinusitis: A Comparison of Systemic Administration of Antibiotic and Antibiotic Delivery by Polylactic Acid Polymer' Laryngoscope (Aug. 1995) vol. 105 pp. 835-842.

Mols, B. 'Moveable Tool Tip for Keyhole Surgery' Delft Outlook (2005) vol. 3 pp. 13-17.

Mooney, M.R. et al 'Monorail™ Piccolino Catheter: A New Rapid Exchange/Ultralow Profile Coronary Angioplasty System' Cathet. Cardiovasc. Diagn. (1990) vol. 20, No. 2 pp. 114-119.

Moriguchi, T. et al 'Addition-Elimination Reaction in the Trifluoroacetylation of Electron-Rich Olefins' J. Org. Chem. (1995) vol. 60, No. 11 pp. 3523-3528. American Chemical Society.

Park, K. et al Biodegreadable Hydrogels for Medicinal Substance Delivery (1993) Technomic Publishing Inc. Lancaster.

Piccirillo, J.F. et al 'Psychometric and Clinimetric Validity of the 20-Item Sino-Nasal Outcome Test (SNOT-20)' Otolaryngol. Head Neck Surg (2002) vol. 126, No. 1 pp. 41-47.

Piers, et al 'A Flexible Distal Tip with Two Degrees of Freedom for Enhanced Dexterity in Endoscopic Robot Surgery' Proceedings 13th Micromechanics Europe Workshop (2002) pp. 271-274.

Podoshin, L. et al 'Balloon Technique for Treatment of Frontal Sinus Fractures' The Journal of Laryngology & Otology (1967), vol. 81. pp. 1157-1161.

Pownell, P.H. et al 'Diagnostic Nasal Endoscopy' Plastic & Reconstructive Surgery (1997) vol. 99, Iss. 5 pp. 1451-1458.

Prince et al 'Analysis of the Intranasal Distribution of Ointment' J Otolaryngol. (1997) vol. 26 pp. 357-360.

Ramsdale, D.R. Illustrated Coronary Intervention A case-oriented approach (2001) Martin Dunitz Ltd. pp. 1-5.

Ritter, F.N. et al Atlas of Paranasal Sinus Surgery (1991) Igaku-Shoin Medical Pub. pp. 1-81.

Robison, J. Mathews, M.D. 'Pressure Treatment of Maxillary Sinusitis' J.A.M.A. (May 31, 1952) pp. 436-440.

Robison, J. Mathews, M.D. 'Pressure Treatment of Purulent Maxillary Sinusitis' TEXAS State Journal of Medicine. (May 1951) pp. 281-288.

Sama, A. et al 'Current Opinions on the Surgical Management of Frontal Sinus Disease' ENT News. www.pinpointmendical.com/ent-news (2009) vol. 17 No. 6 pp. 60-63.

Sanborn, T.A., et al 'Percutaneous Endocardial Transfer and Expression of Genes to the Myocardium Utilizing Fluropscopic Guidance' Catheter Cardiovasc. Interv. (2001) vol. 52, No. 2 pp. 260-266.

Sawbones Catalog 2001, Pacific Research Laboratories, Inc., Vashon, Washington 98070 USA.

Saxon, R.R., et al 'Technical Aspects of Accessing the Portal Vein During the TIPS Procedure' J. Vasc. Interv. Radiol. (1997) vol. 8, No. 5 pp. 733-744.

Schaefer, S.D., M.D. Rhinology and Sinus Disease A Problem-Oriented Approach (Copyright 1988) by Mosby, Inc.

Shah, N.J. et al 'Endoscopic Pituitary Surgery—A Beginner's Guide' Indian Journal of Otolaryngology and Head and Neck Surgery (2004) vol. 56, No. 1 pp. 71-78.

Shah, N.J. 'Functional Endoscopic Sinus Surgery' (1999); found at www.bhj.org/journal/1999_4104_$_{1\ oct99/sp}$_659.htm.

Single-Pole and Multi-Pole Lightguides for UV Spot Light Curing Systems. http://www.dymax.com/products/curing_equipment/lightguids/light. (2004) pp. 1-2.

Sobol, et al 'Sinusitis, Maxillary, Acute Surgical Treatment.' eMedicine. Retrieved from the Internet: <<http://emedicine.medscape.com/article/862030-print>> (Nov. 16, 2010) pp. 1-11.

St. Croix, et al 'Genes Expressed in Human Tumor Endothelium' Science (May 15, 2000) vol. 289 pp. 1197-1202.

Stammberger H. 'Komplikationen entzundlicher Nasennebenhohlenerkrankungen eischließlich iatrogen bedingter Komplikationen.' Eur Arch Oti-Rhino-Laryngol Suppl. (Jan. 1993) pp. 61-102.

Stammberger, et al 'Special Endoscopic Anatomy of the Lateral Nasal Wall and Ethmoidal Sinuses' Functional Endoscopic Sinus Surgery. (1991) Ch. 3, pp. 49-87.

Strohm et al Die Behandlung von Stenosen der oberen Luftwege mittels rontgenologisch gesteuerter Ballondilation (Sep. 25, 1999).

Strohm, et al 'Le Traitement Des Stenoses Voies Aeriennes Superieures Par Dilation Au Balloon' Sep. 25, 1999.

Strohm, et al 'Treatment of the Stenoses of the Upper Air Routes by Balloon Dilation' Sudwestdeutscher (Sep. 25, 1999) Abstract 45 pp. 1-3.

SurgTrainer Product Information 'Incisive Human Nasal Model for ESS Training' Surg Trainer, Ltd. Ibaraki, Japan (2004) http://www1.accsnet.ne.jp/~juliy/st/en/partslist.html.

Tabor, M.H. et al 'Symptomatic Bilateral Nasolacrimal Duct Cysts in a Newborn—Rhinoscopic Clinic' Ear, Nost & Throat Journal (2003) http://findarticles.com/p/articles/mi_m0BUM/is_2_82/ai_98248244 pp. 1-3.

Tarasov, D.I. et al. 'Application of Drugs Based on Polymers in the Treatment of Acute and Chronic Maxillary Sinusitis' Vestn Otorinolaringol. (1978) vol. 6 pp. 45-47.

Terumo. Medi-Tech. Boston Scientific. (1993) Ad for Glidewire.

Weber, R. et al 'Endonasale Stirnhohlenchirugie mit Langzeiteinlage eines Platzhalters' Laryngol. Rhinol. Otol. (1997) vol. 76 pp. 728-734. (English Abstract).

Weber, R. et al 'Videoendscopic Analysis of Nasal Steroid Distribution' Rhinology (1999) vol. 37 pp. 69-73.

Weiner, R.I., D.O. et al 'Development and Application of Transseptal Left Heart Catheterization' Cathet. Cardiovasc. Diagn. (1988) vol. 15, No. 2 pp. 112-120.

Wiatrak, B.J. et al 'Unilateral Choanal Atresia: Initial Presentation and Endoscopic Repair' International Journal of Pediatric Otorhinolaryngology (1998) vol. 46 pp. 27-35.

Woog, et al. 'Paranasal Sinus Endoscopy and Orbital Fracture Repair' Arch Ophthalmol. (May 1998) vol. 116 pp. 688-691.

Wormald, P.J. et al 'The 'Swing-Door' Technique for Uncinectomy in Endoscopic Sinus Surgery' The Journal of Laryngology and Otology (1998) vol. 112 pp. 547-551.

Yamauchi, Y. et al 'Development of a Silicone Model for Endoscopic Sinus Surgery' proc International Journal of Computer Assisted Radiology and Surgery (1999) vol. 99 pp. 1039.

Yamauchi, Y. et al 'A Training System for Endoscopic Sinus Surgery with Skill Evaluation' Computer Assisted Radiology and Surgery (2001) with accompanying copy of poster presentation.

Yanagisawa et al 'Anterior and Posterior Fontanelles.' Ear, Nose & Throat Journal (2001) vol. 80. p. 10-12.

Zimarino, M., MD et al 'Initial Experience with the Europass™: A New Ultra-Low Profile Monorail Balloon Catheter' Cathet. Cardiovasc. Diagn. (1994) vol. 33, No. 1 pp. 76-79.

http://www.invotec.net/rhinology/ksplint.html. K-Splint Internal Nasal Splints; Jan. 25, 2007.

http://www.doylemedical.com/nasalsplints.htm; Doyle Nasal Splints; Jan. 25, 2007.

http://www.technologyforlife.com.au/ent/nasal.html; Nasal Surgery and Accessories; Jan. 25, 2007.

EP Communication dated Sep. 4, 2008 re: EP 05773189.
EP Communication dated Jun. 19, 2009 re: EP 05773189.
Examination Report dated Feb. 22, 2006 re: 02716734.5.
Examination Report dated Feb. 8, 2007 re: 02716734.5.
Examiners First Report dated Apr. 8, 2010 re: AU2005274794.
European Search Report and Search Opinion dated Sep. 11, 2009 from EP06815174.
European Search Report dated Sep. 27, 2011 re: EP10182961.
International Preliminary Report on Patentability dated Aug. 25, 2006 from PCT/US05/25371.
International Preliminary Report on Patentability dated Oct. 4, 2007 from PCT/US06/002004.
International Preliminary Report on Patentability dated Nov. 27, 2008 from PCT/US07/11449.
International Preliminary Report on Patentability dated Apr. 16, 2009 from PCT/US07/021170.
International Preliminary Report on Patentability dated May 14, 2009 from PCT/US06/36960.
International Preliminary Report on Patentability dated Oct. 22, 2009 from PCT/US08/059786.
International Preliminary Report on Patentability dated Nov. 5, 2009 from PCT/US08/061343.
International Search Report dated May 23, 2002 from PCT/EP02/01228.
International Search Report and Written Opinion dated Apr. 10, 2006 from PCT/US05/25371.
International Search Report dated May 8, 2007 from PCT/US2006/16026.
International Search Report and Written Opinion dated Aug. 17, 2007 from PCT/US05/13617.
International Search Report and Written Opinion dated Aug. 29, 2007 from PCT/US06/002004.
International Search Report dated Sep. 25, 2007 from PCT/US06/37167.
International Search Report dated Oct. 19, 2007 from PCT/US07/03394.
International Search Report and Written Opinion dated May 29, 2008 from PCT/US07/021170.
International Search Report dated May 29, 2008 from PCT/US07/21922.
International Search Report and Written Opinion dated Jul. 1, 2008 from PCT/US06/22745.
International Search Report dated Jul. 3, 2008 from PCT/US2006/029695.
International Search Report dated Jul. 7, 2008 from PCT/US07/16213.
International Search Report dated Jul. 8, 2008 from PCT/US07/11474.
International Search Report and Written Opinion dated Jul. 17, 2008 from PCT/US06/36960.
International Search Report and Written Opinion dated Jul. 21, 2008 from PCT/US05/33090.
International Search Report dated Aug. 25, 2008 from PCT/US2008/000911.
International Search Report dated Sep. 10, 2008 dated PCT/US07/16212.
International Search Report and Written Opinion dated Sep. 12, 2008 from PCT/US07/16214.
International Search Report and Written Opinion dated Sep. 17, 2008 from PCT/US08/059786.
International Search Report and Written Opinion dated Sep. 17, 2008 from PCT/US08/061343.
International Search Report and Written Opinion dated Oct. 1, 2008 from PCT/US07/11449.
International Search Report dated Oct. 15, 2008 from PCT/US2008/061048.
International Search Report dated Nov. 30, 2009 re: PCT/US2009/057203.
International Search Report from PCT Application No. PCT/US2009/057203 dated Nov. 30, 2009 as issued by the European Patent Office as searching authority.
International Search Report dated Dec. 10, 2009 re: PCT/US2009/052236.
International Search Report dated Dec. 16, 2009 re: PCT/US2009/050800.
International Search Report dated Mar. 31, 2010 re: PCT/US2009/069143.
International Search Report dated Jul. 8, 2010 re: PCT/US2010/027837.
International Search Report dated Oct. 6, 2010 re: PCT/US2010/040548.
International Search Report dated Mar. 25, 2011 re: PCT/US2010/062161.
International Search Report dated Mar. 28, 2011 re: PCT/US2010/061850.
International Search Report dated Mar. 31, 2011 re: PCT/US2010/060898.
International Search Report dated Aug. 9, 2011 re: PCT/US2011/038751.
Partial European Search Report dated Sep. 20, 2007 re: 07252018.
Partial European Search Report dated Feb. 7, 2012 re: PCT/US2011/052321.
Supplemental European Search Report dated Jun. 2, 2008 re: EP05773189.
Supplemental European Search Report dated Jul. 1, 2009 re: EP06815285.
Supplemental European Search Report dated Jan. 29, 2010 from EP07836108.
Supplemental European Search Report dated Feb. 2, 2010 re: EP07826109.
Supplemental European Search Report dated Feb. 17, 2010 re: EP07836110.
Supplemental European Search Report dated Mar. 1, 2010 re: EP05778834.
Supplemental European Search Report dated Mar. 16, 2010 from EP06718986.
Supplemental European Search Report dated Jun. 22, 2010 re: EP06784759.
Supplemental European Search Report dated Sep. 23, 2010 re: EP08746715.
Supplemental Partial European Search Report dated Nov. 19, 2010 re: EP06751637.
Supplemental European Search Report dated Jan. 28, 2011 re: 07777004.
Supplemental European Search Report dated Mar. 31, 2011 re: EP05798331.
Supplemental European Search Report dated Aug. 30, 2011 re: EP06800540.
Supplemental European Search Report dated Sep. 29, 2011 re: EP 07750248.
U.S. Appl. No. 10/259,300, filed Sep. 30, 2002.
U.S. Appl. No. 10/259,630, filed Sep. 30, 2002.
U.S. Appl. No. 10/470,881, filed Feb. 4, 2004.
U.S. Appl. No. 10/829,917, filed Apr. 21, 2004.
U.S. Appl. No. 10/912,578, filed Aug. 4, 2004.
U.S. Appl. No. 10/944,270, filed Sep. 17, 2004.
U.S. Appl. No. 11/037,548, filed Jan. 18, 2005.
U.S. Appl. No. 11/116,118, filed Apr. 26, 2005.
U.S. Appl. No. 11/150,847, filed Jun. 10, 2005.
U.S. Appl. No. 11/193,020, filed Jul. 29, 2005.
U.S. Appl. No. 11/234,395, filed Sep. 23, 2005.

U.S. Appl. No. 11/347,147, filed Feb. 2, 2006.
U.S. Appl. No. 11/355,512, filed Feb. 16, 2006.
U.S. Appl. No. 11/436,892, filed May 17, 2006.
U.S. Appl. No. 11/436,897, filed May 17, 2006.
U.S. Appl. No. 11/438,090, filed May 18, 2006.
U.S. Appl. No. 11/522,497, filed Sep. 15, 2006.
U.S. Appl. No. 11/527,773, filed Sep. 25, 2006.
U.S. Appl. No. 11/544,009, filed Oct. 4, 2006.
U.S. Appl. No. 11/647,530, filed Dec. 27, 2006.
U.S. Appl. No. 11/648,159, filed Dec. 29, 2006.
U.S. Appl. No. 11/655,794, filed Jan. 18, 2007.
U.S. Appl. No. 11/725,151, filed Mar. 15, 2007.
U.S. Appl. No. 11/789,704, filed Apr. 24, 2007.
U.S. Appl. No. 11/789,705, filed Apr. 24, 2007.
U.S. Appl. No. 11/803,695, filed May 14, 2007.
U.S. Appl. No. 11/925,540, filed Oct. 26, 2007.
U.S. Appl. No. 11/926,326, filed Oct. 29, 2007.
U.S. Appl. No. 11/926,565, filed Oct. 29, 2007.
U.S. Appl. No. 11/928,097, filed Oct. 30, 2007.
U.S. Appl. No. 12/011,100, filed Jan. 23, 2008.
U.S. Appl. No. 12/100,361, filed Apr. 9, 2008.
U.S. Appl. No. 12/117,582, filed May 8, 2008.
U.S. Appl. No. 12/117,672, filed May 8, 2008.
U.S. Appl. No. 12/117,961, filed May 9, 2008.
U.S. Appl. No. 12/118,931, filed May 12, 2008.
U.S. Appl. No. 12/120,902, filed May 15, 2008.
U.S. Appl. No. 12/122,884, filed May 19, 2008.
U.S. Appl. No. 12/340,226, filed Dec. 19, 2008.
U.S. Appl. No. 12/341,602, filed Dec. 22, 2008.
U.S. Appl. No. 12/502,101, filed Jul. 13, 2009.
U.S. Appl. No. 60/844,874, filed Sep. 15, 2006.
U.S. Appl. No. 60/922,730, filed Apr. 9, 2007.
U.S. Appl. No. 61/052,413, filed May 12, 2008.
U.S. Appl. No. 61/084,949, filed Jul. 30, 2008.
USPTO Office Action dated Sep. 16, 2005 in U.S. Appl. No. 10/259,300.
USPTO Office Action dated Jul. 7, 2006 in U.S. Appl. No. 10/259,300.
USPTO Office Action dated Feb. 13, 2007 in U.S. Appl. No. 10/259,300.
USPTO Office Action dated May 29, 2007 in U.S. Appl. No. 10/912,578.
USPTO Office Action dated Oct. 9, 2007 in U.S. Appl. No. 10/259,300.
USPTO Office Action dated Oct. 18, 2007 in U.S. Appl. No. 11/037,548.
USPTO Office Action dated Nov. 14, 2007 in U.S. Appl. No. 10/912,578.
USPTO Office Action dated Nov. 28, 2007 in U.S. Appl. No. 11/234,395.
USPTO Office Action dated Dec. 6, 2007 in U.S. Appl. No. 11/037,548.
USPTO Office Action dated Dec. 10, 2007 in U.S. Appl. No. 10/912,578.
USPTO Office Action dated Jan. 24, 2008 in U.S. Appl. No. 10/259,300.
USPTO Office Action dated Apr. 9, 2008 in U.S. Appl. No. 11/037,548.
USPTO Office Action dated Sep. 12, 2008 in U.S. Appl. No. 10/829,917.
USPTO Office Action dated Oct. 6, 2008 in U.S. Appl. No. 10/259,300.
USPTO Office Action dated Oct. 29, 2008 in U.S. Appl. No. 11/347,147.
USPTO Office Action dated Nov. 7, 2008 in U.S. Appl. No. 10/944,270.
USPTO Office Action dated Nov. 17, 2008 in U.S. Appl. No. 10/829,917.
USPTO Office Action dated Nov. 17, 2008 in U.S. Appl. No. 12/117,582.
USPTO Office Action dated Nov. 17, 2008 in U.S. Appl. No. 12/118,931.
USPTO Office Action dated Nov. 25, 2008 in U.S. Appl. No. 12/117,961, filed May 9, 2008.
USPTO Office Action dated Dec. 5, 2008 in U.S. Appl. No. 12/120,902, filed May 15, 2008.
USPTO Office Action dated Jan. 28, 2009 in U.S. Appl. No. 10/944,270.
USPTO Office Action dated Feb. 4, 2009 in U.S. Appl. No. 11/347,147.
USPTO Office Action dated Mar. 3, 2009 in U.S. Appl. No. 12/117,582.
USPTO Office Action dated Mar. 4, 2009 in U.S. Appl. No. 12/118,931.
USPTO Office Action dated Mar. 17, 2009 in U.S. Appl. No. 11/690,127.
USPTO Office Action dated Mar. 18, 2009 in U.S. Appl. No. 10/829,917.
USPTO Office Action dated Mar. 23, 2009 in U.S. Appl. No. 11/804,309.
USPTO Office Action dated Mar. 23, 2009 in U.S. Appl. No. 11/926,326.
USPTO Office Action dated Apr. 21, 2009 in U.S. Appl. No. 10/944,270.
USPTO Office Action dated Jul. 30, 2009 in U.S. Appl. No. 12/118,931.
USPTO Office Action dated Aug. 6, 2009 in U.S. Appl. No. 11/347,147.
USPTO Office Action dated Aug. 6, 2009 in U.S. Appl. No. 12/117,582.
USPTO Office Action dated Aug. 6, 2009 in U.S. Appl. No. 12/117,961.
USPTO Office Action dated Aug. 28, 2009 in U.S. Appl. No. 11/150,847.
USPTO Office Action dated Oct. 21, 2009 in U.S. Appl. No. 12/120,902.
USPTO Office Action dated Nov. 9, 2009 in U.S. Appl. No. 10/829,917.

* cited by examiner

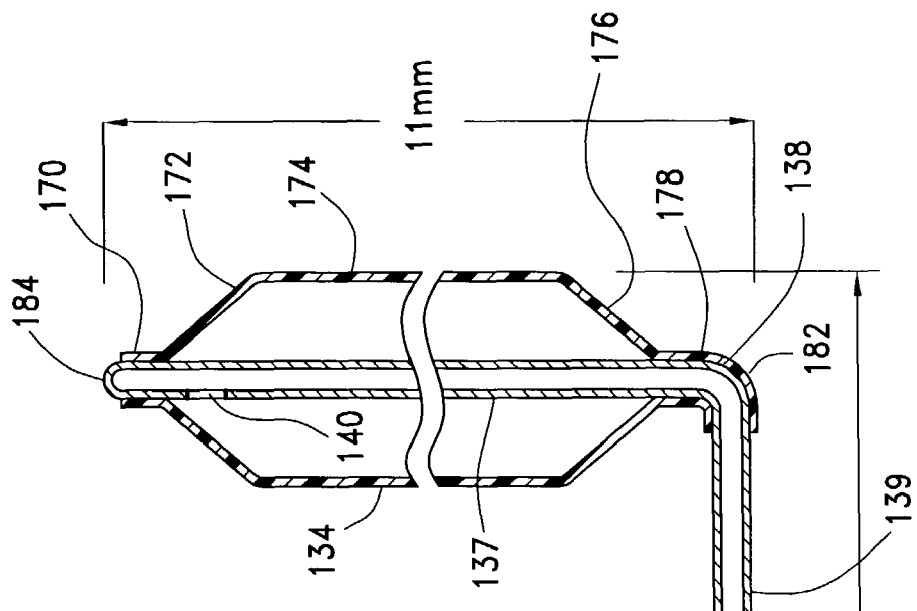
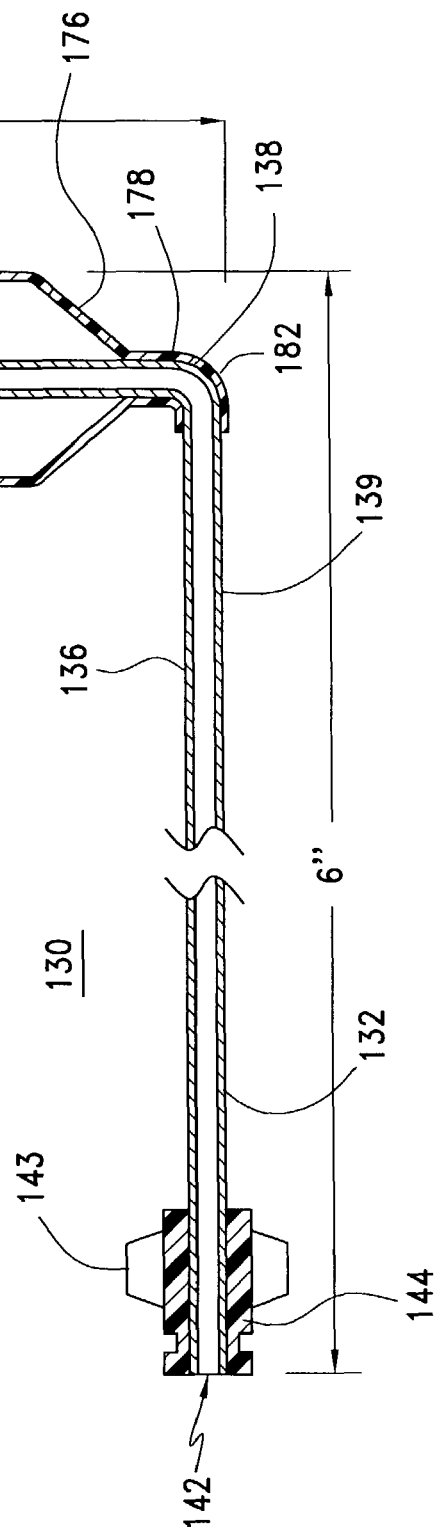
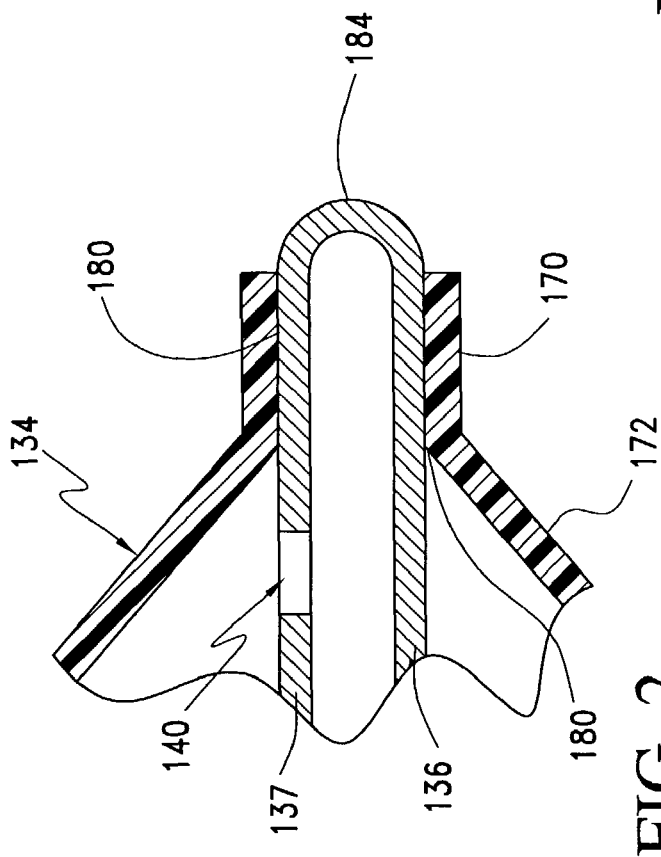
FIG. 1
FIG. 2

BALLOON CATHETERS AND METHODS
FOR TREATING PARANASAL SINUSES

FIELD OF THE INVENTION

This invention relates to balloon catheters and methods using such catheters for treating paranasal sinuses.

BACKGROUND AND DESCRIPTION OF THE PRIOR ART

To fully understand the invention, it is necessary to consider the anatomy and physiology of the sinus system. FIGS. 4-16, which show various steps of methods of the invention, also show important features of sinus anatomy. The maxillary sinus 21 lies lateral to the nasal cavity 38, inferior to the eye orbit 23 and superior to the palate or roof of the mouth. The medial wall of the maxillary sinus forms the lateral nasal wall 44 inferiorly. The frontal sinus 35 (FIG. 16) lies above the orbit and its floor is formed by the frontal bone and is contiguous with part of the orbital roof. The right and left frontal sinuses are divided by the interfrontal septum. The frontal sinus drains into the nasal cavity and its outflow tract is in the inferomedial sinus, which connects to the frontonasal duct 36. Frontonasal duct 36 empties into the nasal cavity through lateral nasal wall 44 under the middle turbinate 20.

The ethmoid sinus is divided into anterior and posterior ethmoid air cells 29 and 31. The ethmoid sinus consists of multiple spaces or cells divided by thin bony septae. The ethmoid sinus is contained in the ethmoid bone. The lateral wall of the ethmoid sinus composes the medial wall of the orbit. The medial wall of the ethmoid sinus composes the lateral wall 44 of the nasal cavity superiorly. Anterior ethmoid air cells 29 drain through lateral nasal wall 44 into the middle meatus 22 beneath middle turbinate 20.

The sphenoid sinus 39 is posterior to the ethmoid sinus 29 and 31. Sphenoid sinus 39 has a lateral wall that is adjacent to the optic nerve, carotid artery, and cavernous sinus. The floor of sphenoid sinus 39 lies above maxillary sinus 21 and pterygopalatine fossa. Lateral nasal wall 44 is partially covered by inferior 46, middle 20, and superior 17 turbinates.

Sinus physiology will now be considered. The mucosa of nasal cavity 38 contains secretory elements (mucosal glands and goblet cells) and a dense ciliary layer. The paranasal sinuses are covered by a similar mucosa, although the secretory cells and cilia may be sparser in the more remote areas of the sinuses. The secretory cells produce a large volume of mucus that is normally actively transported by the cilia (mucociliary transport) in a specific pattern (not a gravity dependant pattern) from the sinus through the opening between the sinus and the nasal cavity (sinus ostium). Cellular debris and bacteria are transported in the mucus from the sinus cavity through the ostium into the nose.

Inflammation of the sinus and nasal mucosa causes hyperemia, lymphatic swelling, stasis in the blood and lymphatic pathways and leads to increased secretion of mucus and reduced mucociliary transport. The inflammation may be caused by allergies, noxious agents, nasal polyps, and other factors. Over time there is a pathologic increase in inflammatory cells, ground substance, and fibers with a permanent disruption of mucociliary transport and lymphatic drainage. An obstruction of the narrow ducts and ostia between the paranasal sinuses and nasal cavity develops, resulting in a vicious cycle of increased secretions, edema, and ultimately organized connective tissue and mucosal hyperplasia. Bacteria are not cleared from the sinuses and multiply in the fertile inflammatory environment worsening the chronic sinus inflammation (sinusitis).

Treatment with antibiotics, corticosteroids in nasal sprays or systemically, and antihistamines may result in resolution of sinusitis. However some patients become resistant to medical treatment and surgery becomes necessary.

Modern sinus surgery is usually performed endoscopically and is based on the principle of restoring patency of the sinus ducts and ostia by enlarging the opening and allowing mucociliay clearance of mucus from the sinus into the nose to resume. If mucociliary clearance is re-established, then the inflammatory changes in the sinus mucosa described above will resolve. In classic sinus surgery, an incision was made along the side of the nose in the medial canthus to access the ethmoid or sphenoid sinuses. This incision could be extended to beneath the medial half of the brow to also access the frontal sinus. An incision through the gums above the upper teeth and creation of a large bony opening in the maxilla with excision of large areas of sinus mucosa was used to perform maxillary sinus surgery. A large opening was created through the medial wall of the maxillary sinus into the nose in the inferior meatus (maxillary antrostomy) to allow postoperative drainage of the sinus.

The development of endoscopic sinus surgery allowed sinus surgery to be performed from an intranasal approach, thus eliminating the need for external incisions, the creation of very large bony openings, and reducing morbidity. However, endoscopic sinus surgery requires the excision of large areas of bone and nasal mucosa and has reported complications of blindness from damage to the optic nerve, double vision from damage to the orbit and medial rectus muscle, damage to the nasolacrimal duct resulting in tearing and dacryocstitis, leakage of central nervous system fluid and infection of the brain and meninges, loss of the sense of taste, and pain and neuralgia of the face and scalp, and infection of the skull base.

As shown in U.S. Pat. Nos. 5,021,043 and 5,169,386, I have previously co-invented balloon catheters for use in the lacrimal system. In my application "Transnasal Method and Catheter for Lacrimal System," filed herewith, I teach that a balloon catheter can be introduced transnasally to treat the lacrimal system.

A review of the prior art shows a number of patents (Katz U.S. Pat. No. 6,027,478; Brennan U.S. Pat. No. 4,883,465; Akiyama U.S. Pat. No. 4,102,342; Payton U.S. Pat. No. 4,338,941; Katz U.S. Pat. No. 5,454,817; Stangerup U.S. Pat. No. 5,546,964 and Shippert U.S. Pat. No. 5,827,224) which teach the use of expandable devices (usually a balloon) into the nasal cavity or sinuses. Most of these are for the treatment of nose bleeds or the control of bleeding.

A number of articles disclose the use of a balloon catheter in sinuses to hold fractured bones in place, stop bleeding by tamponade, prevent fluid from flowing out of the nose into the pharynx, or to maintain a low intranasal air pressure. In one case, a catheter was used to stent a duct after surgery; and the balloon was inflated in the sinus to deep the stent in position. However, there are no teachings in the prior are to use a balloon catheter to create a new opening from a sinus into the nose, to dilate an ostium or duct, or excise a sinus. A balloon was never used to directly treat sinus disease.

SUMMARY OF THE INVENTION

The present inventions teaches the use of sinus balloon catheters to treat sinus disease by creating a new opening from a sinus into the nose, to dilate a sinus ostium or duct, or to excise a sinus. The balloon catheters of the invention constitute a set of catheters having different configurations and dimensions suitable for the treatment of different parts of the paranasal sinus system. The catheters comprise a hypotube formed of stainless steel of sufficient stiffness and column strength to be pushed through a surgically prepared small, tight opening from a sinus into the nose, through a sinus ostium or duct, or into a sinus cavity. The small opening may be created surgically or may be the natural ostium or duct of the sinus.

One of the balloon catheters used in the invention has a proximal segment and a circular bend placing a distal segment at an angle of 70° to 115°, preferably 90° to the proximal segment. A balloon is mounted over the distal segment which has a slot permitting a fluid under the pressure applied to the proximal end of the proximal segment to inflate the balloon.

The angled distal segment allows the surgeon to rotate or shift the position of the long proximal catheter shaft, thus positioning the distal segment to enter from the nasal cavity into the sinus at various angles appropriate to each individual patient. The balloon catheter with the 90 degree angle is used to treat maxillary and frontal sinus disease.

The distal segment of the balloon catheter from the outside of the bend to the end of the catheter is 14 mm. The length of the distal segment is short enough to allow it to be rotated within the nasal cavity and thus enter from the nasal cavity into the sinus at the desired angle. The distal segment is long enough to allow a balloon of sufficient length and diameter to be attached to the hypotube for dilation of an opening through the lateral nasal and sinus wall, duct, or ostium. The balloon material is attached with adhesive to the very distal portion of the distal segment and to the proximal portion of the distal segment, the bend, and the very distal portion of the long proximal segment. A longer working segment of balloon can be used because the area of adhesion of the balloon includes the bend and the distal portion of the proximal segment. A 9 mm inflated diameter angled balloon is used to treat the maxillary sinus and a 5 mm inflated diameter angled balloon is to treat the frontal sinus.

Another balloon catheter of the invention is straight or has a minimal angle at the junction of the distal segment and the proximal segment. This balloon catheter is used for ethmoidectomy and sphenoid sinusotomy and uses a balloon with an inflated diameter of 9 mm. Each of the balloon catheters of the invention have a sufficiently small deflated profile to fit through the sinus ostium, duct, or opening in the nasal wall or scar tissue into the sinus.

It is useful to apply a lubricious coating to the balloon material to facilitate pushing it through the lateral nasal wall and sinus wall into the sinus. The proximal catheter shaft has a luer lock with wings or an expansion to allow the catheter to be attached to tubing from the inflation device. The wings allow the surgeon to more easily manipulate the balloon catheter.

The methods of the invention open or enlarge an obstructed or narrowed ostium or duct of a sinus using a balloon and allow the sinus to drain into the nose. This is accomplished without causing damage to the surrounding structures such as the optic nerve, extraocular muscles that move the eye, the orbit, brain, meninges, or nasolacrimal duct.

Another method of the invention removes a sinus and cures sinus disease without damage to the surrounding structures such as the optic nerve, extraocular muscles, orbit, brain, meninges, and nasolacrimal duct. The methods of the invention are useful for opening a sinus ostium or duct which has been narrowed or obstructed by scar tissue from previous surgery or trauma, for creating a new opening in the wall of a sinus which has scar tissue to allow proper drainage of the sinus into the nose, and for removing a sinus which has scar tissue.

The methods of the invention include a balloon catheter antrostomy of the maxillary ostium, a balloon catheter middle meatal maxillary antrostomy, a balloon catheter inferior meatal antrostomy, a balloon catheter ethmoidectomy of the anterior ethmoid sinus, a balloon catheter ethmoidectomy of the posterior ethmoid sinus, a balloon catheter sinusotomy of the sphenoid sinus, and a balloon catheter frontal sinusotomy.

BRIEF DESCRIPTION OF THE DRAWINGS

FIG. 1 is a schematic drawing of one embodiment of the sinus balloon catheter of the invention;

FIG. 2 is a closeup schematic drawing of the tip of the distal segment of the sinus balloon catheter of FIG. 1;

DETAILED DESCRIPTION

Figure 3A:
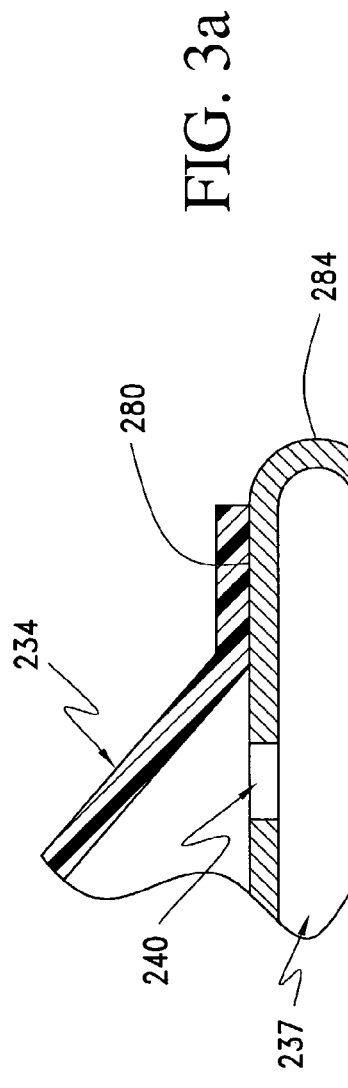
FIG. 3a is a closeup schematic drawing of the tip of the sinus balloon catheter of FIG. 3.

As shown in FIGS. 1 and 2, a first embodiment of a sinus balloon catheter 130 of the invention is assembled from a tube 136, preferably a stainless steel hard tempered hypotube which has a circular bend 138 of 0.13" radius such that distal segment 137 is oriented 70° to 115°, preferably 90°, to proximal segment 139. A slot 140 is provided in segment 137. The distance from the distal tip 184 of distal segment 137 to the outer wall of proximal segment 139 of hypotube 136 is 4 mm to 30 mm, preferably 14 mm, as shown in FIG. 1. The distal tip 184 of the hypotube 136 is closed, whereas the proximal end 142 is open. However, the lumen of tube 136 may be closed in distal segment 137, up to 10 mm from distal tip 184, allowing distal tip 184 to remain open. In either case, tube 136 is closed distally of slot 140. The proximal end 142 of hypotube 136 is inserted into a mold for forming luer 144 and plastic is injected into the mold to form luer 144 attached to the end of proximal segment 139. The inner diameter of the luer 144 matches the external diameter of the hypotube 136. The luer 144 has wings 143 or other enlargement or expansion on it to enable the surgeon to better hold and manipulate balloon catheter 130. Catheter 130 is 4" to 10" long, preferable 6" in length as measured from proximal end 142 to distal tip 184, as shown in FIG. 1. The wall 132 of tube 136 should be of such thickness that the tube has sufficient stiffness and column strength with marked resistance to lateral bending that distal segment 137 can be pushed through a prepared small, tight opening from a sinus into the nose, pushed through a sinus ostium or duct, or pushed into a sinus cavity which may require considerable pressure in some cases. It has been found that a tube with a wall thickness of at least 0.035 inch will be satisfactory. A preferred tube has an outer diameter of 0.083" and an inner diameter of 0.039" with a wall thickness of 0.044".

Port 140 in distal segment 137 is formed by inserting temporarily a discardable wire segment into the tube 136. This is done before inserting hypotube 136 into luer 144. A transverse slot is cut in the tube 136 approximately 2 mm to 14 mm, preferably 4 mm, from its distal end 184 to form port 140. The slot extends in depth to approximately one third of the diameter of tube 136. A wire wheel is used to remove any burrs, and the discardable core wire is removed and discarded.

A balloon 134 is preferably formed of polyethylene terephthalate and has a length of approximately 4 mm to 30 mm, preferably 14 mm, and a working inflated diameter of 2 mm to 14 mm, preferably 9 mm, for use in the sinus system, except for use in the nasofrontal duct where the preferable inflated working diameter is 5 mm. The balloon has a distal neck 170, a distal tapered region 172, a center region 174, a proximal tapered region 176, and a proximal neck 178. During installation, tube 136 is cleaned with isoproponol and then coated with a primer, "Loctite 770." The balloon is placed over the distal end of tube 136 to align the distal end of distal neck 170 with distal end 184 of tube 136. An adhesive, such as cyanoacrylate, is used. An acceptable adhesive "Loctite 4081" is available from Loctite Corporation. The adhesive is applied to distal end of distal neck 170 and the proximal end of proximal neck 178 to form bonds 180 and 182, respectively. The adhesive is applied to the balloon necks 170, 178 using a small mandrel such as a wire approximately 0.010" to 0.014" in diameter. The adhesive wicks into the necks due to capillary action. Proximal neck 178 may be bonded on distal segment 137 of tube 136 or extend over bend 138 onto the distal end portion of proximal segment 139 of tube 136. Extension of the proximal neck 178 onto bend 138 and proximal segment 139 allows a greater length of the working diameter, i.e., center region 174, to be on distal segment 137 of tube 136.

Figure 3:
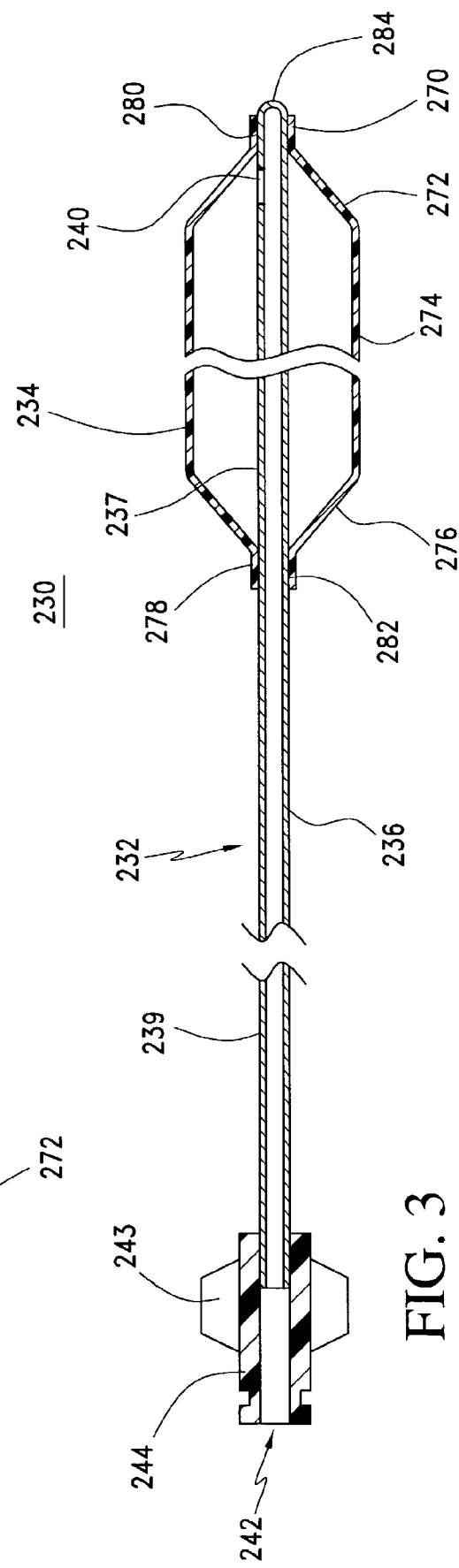
FIG. 3 is a schematic drawing of a second embodiment of a sinus balloon catheter of the invention.

A second embodiment of sinus catheter of the invention is shown in FIG. 3. The catheter 230 is assembled from a tubular body 232, formed of stainless steel hard tempered hypotube 236 which is straight or has a mild circular bend distally such that distal segment 237 is oriented 130 to 180, preferably 180°, to a long proximal segment 239. The distance from the distal tip 284 of distal segment 237 to the outer wall of proximal segment 239 of hypotube 236 is 10 to 100 mm, preferably 16 mm. The distal tip 284 of the hypotube 236 preferably is closed whereas the proximal end 242 is open. However, the lumen of tube 236 may be closed 0 to 10 mm from distal tip 284 allowing distal tip 284 to be open. The proximal end 242 of hypotube 236 is inserted into a mold for forming luer 244. Heated plastic is injected into the mold to form luer 244 attached to the end of proximal segment 239. The inner diameter of luer 244 matches the external diameter of hypotube 236. The luer 244 has wings 243 or expansions on it to enable the surgeon to better hold and manipulate balloon catheter 230.

Catheter 230 has a port 240 in distal segment 237 which is formed by inserting temporarily a discardable wire segment into the tube 236. This is done before inserting hypotube 236 into luer 244. A transverse slot is cut in tube 236 approximately 2 to 14 mm, preferably 4 mm, from its distal end 284 to form port 240. The slot extends in depth to approximately ⅓ of the diameter of tube 236. A wire wheel is used to remove any burrs, and the discardable core wire is removed and discarded.

It is desirable for the catheter 230 to have column strength and marked resistance to lateral bending. The deflated catheter must be capable of being pushed through an initial prepared small opening in the nasal or sinus wall, an ostium or duct, and into a sinus cavity. This may require considerable pressure in some cases.

A balloon 234, preferably formed of polyethylene terephthalate, has a length of approximately 4 to 30 mm, preferably 14 mm, and an inflated working diameter of 3 to 15 mm, preferably 9 mm. The balloon has a distal neck 270, a distal tapered region 272, a center region 274, a proximal tapered region 276, and a proximal neck 278. Necks 270 and 278 are bonded to hypotube 236, forming bonds 280 and 282, in the same manner as is described above with respect to the attachment of necks 178 and 170 to hypotube 136.

As will be described below, angled catheter 130 and "straight" catheter 230 will be used in different method steps for treating various prepared openings, naturally occurring ostia and ducts, and sinus cavities. It is also to be noted that dimensions of the catheters are selected to accommodate different conditions in the paranasal sinus system. For example, the outer diameters of the distal segments with the balloon deflated are selected so that the respective distal segments with the balloon deflated will fit snugly with the prepared openings, natural ostia or ducts and sinus cavities into which these distal segments are to be pushed. As already mentioned, the working inflated diameters of the balloons differ depending on the size required to treat different parts of the paranasal sinus system. Accordingly, the surgeon must, at the time surgery is begun, have available a set of sinus balloon catheters which are angled or straight, the balloons of which have appropriate inflated working diameters, and which have appropriate outer diameters with the balloon deflated that will enable the catheter in question to be pushed into the respective prepared opening, natural ostium or duct or sinus cavity to be excised.

Figure 4:
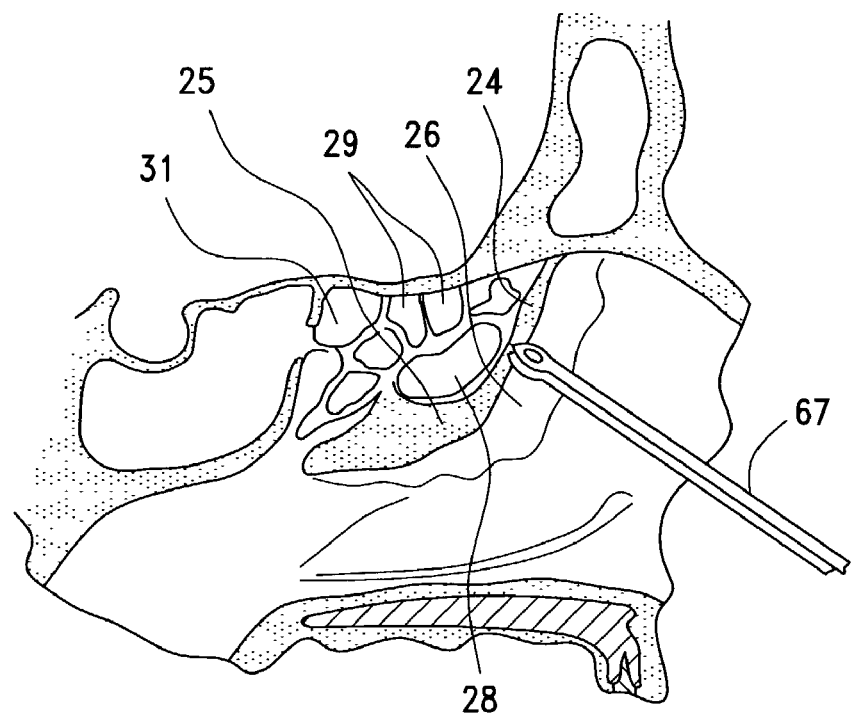
FIG. 4 is a schematic drawing of a step of a method of the invention, showing the uncinate process being removed with a punch to expose the ethmoid infundibulum and semilunar hiatus.
Figure 5:
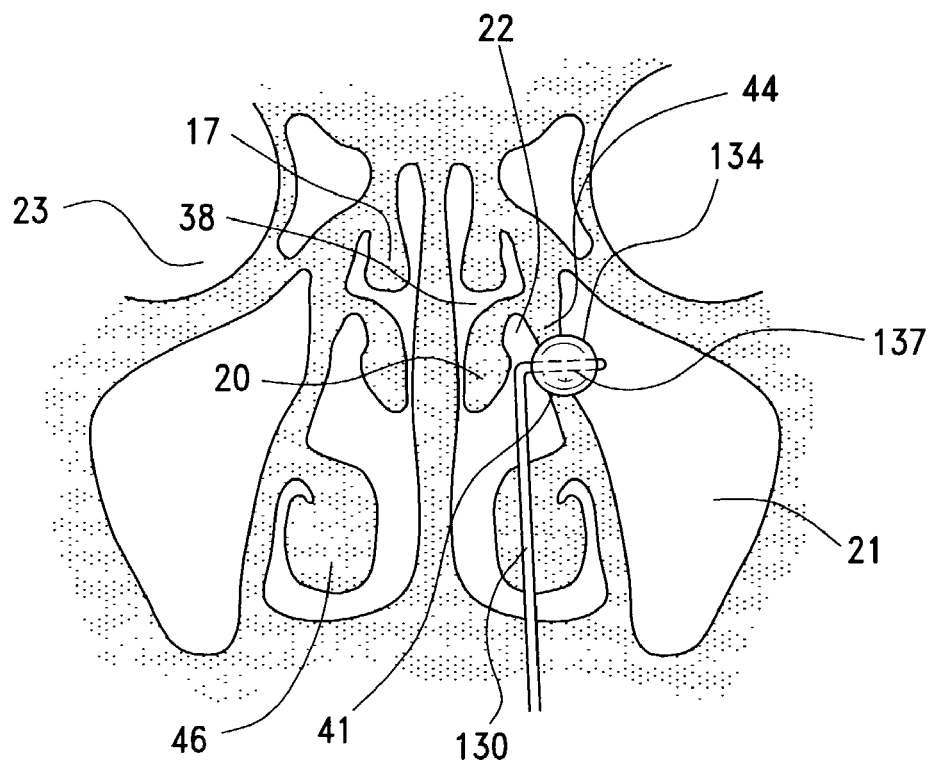
FIG. 5 is a schematic drawing of another step of the method of FIG. 4 showing the sinus balloon catheter dilating and thereby enlarging the ostium of the maxillary sinus.

Turning to FIGS. 4 and 5, in a method of performing balloon catheter antrostomy of the maxillary ostium, the middle turbinate 20 is retracted medially to gain access to the middle meatus 22. In some cases the middle turbinate is resected. The ethmoid infundibulum 24 is exposed by using cutting forceps 67 to remove part of the uncinate process 26 (FIG. 4). Distal segment 137 of balloon catheter 130 is then pushed through the maxillary ostium 41 (which is in ethmoid infundibulum 24) into the maxillary sinus 21. As seen in FIG. 5, balloon 134 is inflated to 9 bars (atmospheres) for 20 seconds then deflated. Distal segment 137 of balloon catheter 130 is slightly repositioned to insure full dilation and inflated again to 9 bars for 20 seconds. Balloon 134 is then deflated, and catheter 130 is removed from the now enlarged ostium 41.

Figure 6:
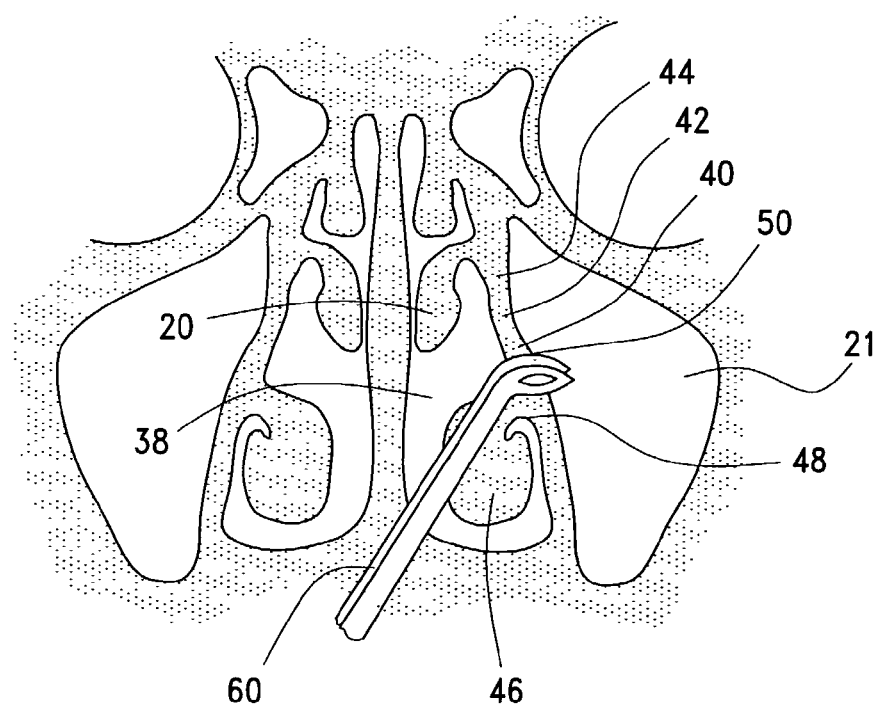
FIG. 6 is a schematic drawing of a step of a second method of the invention showing the Blakesely punch creating a small opening in the fontanelle of the lateral nasal wall in the middle meatus thus creating a communication between the maxillary sinus and nasal cavity.
Figure 7:
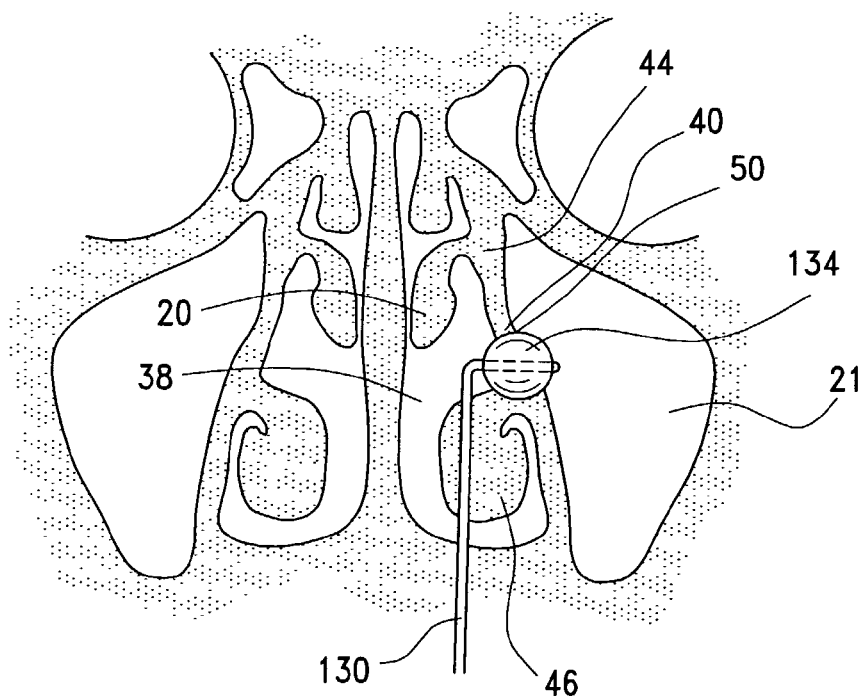
FIG. 7 is a schematic drawing of another step of the method of FIG. 6 showing the sinus balloon catheter dilating the opening in the fontanelle of the lateral nasal wall in the middle meatus thus creating a large communication opening (antrostomy) for drainage from the maxillary sinus into the nasal cavity.

Turning to FIGS. 6 and 7, in a method of performing a middle meatal maxillary antrostomy, an initial opening is made in the fontanelle 40 (section of thin membranous tissue without bone of the medial maxillary sinus wall 42 which is also a portion of the lateral nasal wall 44). This is performed by bringing a 45 degree upbiting Blakesely punch 60 into nasal cavity 38 along the lateral nasal wall 44 just superior to the inferior turbinate 46 at the midpoint of its horizontal axis to perforate fontanelle 40 to create a new 3 mm opening 50 (FIG. 6). The punch 60 is removed, and sinus balloon catheter 130 is brought into nasal cavity 38 and pushed into the new opening 50 in fontanelle 40 of lateral nasal wall 44 (FIG. 7). Balloon 134 is inflated to 9 bars for 20 seconds then deflated. Balloon catheter 130 is slightly repositioned in the enlarged opening 50 to insure thorough dilation and inflated again to 9 bars for 20 seconds. Balloon catheter 130 is then deflated and withdrawn from opening 50 and nasal cavity 38.

Figure 8:
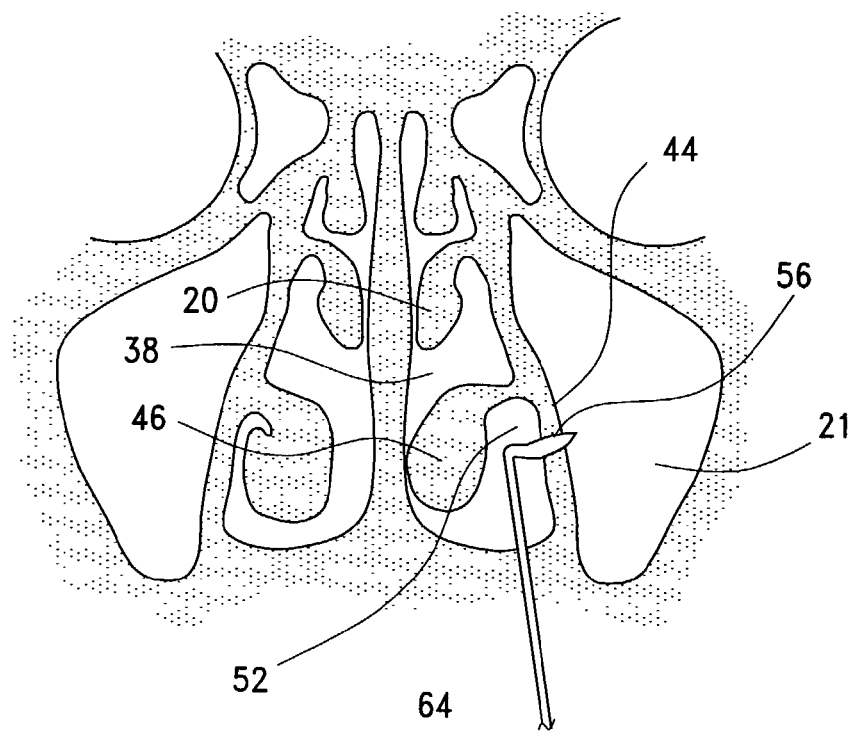
FIG. 8 is a schematic drawing of a step of a third method of the invention showing the dissector perforating the lateral nasal wall in the inferior meatus into the maxillary sinus.
Figure 9:
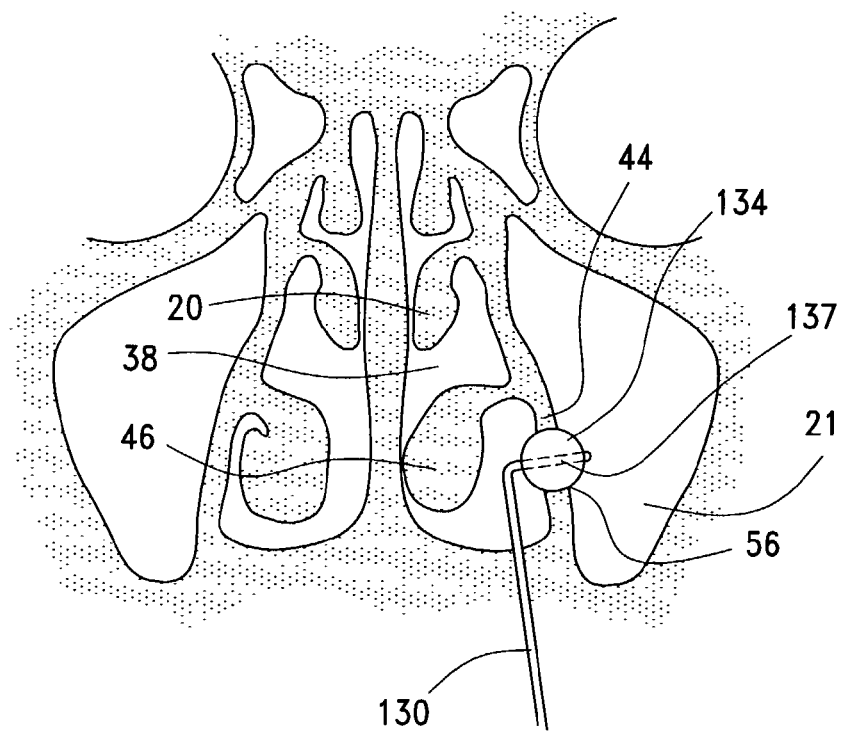
FIG. 9 is a schematic drawing of another step of the method of FIG. 8 showing the sinus balloon catheter dilating the opening in the lateral nasal wall in the inferior meatus thus creating a large antrostomy for drainage from the maxillary sinus into the nasal cavity.

As seen in FIGS. 8 and 9, in a method of inferior meatal antrostomy, the inferior turbinate 46 has been displaced medially. A sharp dissector 64 is introduced into nasal cavity 38 and used to perforate lateral nasal wall 44 in the inferior meatus 52 to create an opening 56 in lateral nasal wall 44 (FIG. 8). Dissector 64 is withdrawn from nasal cavity 38. The deflated balloon catheter 130 is introduced into the nasal cavity 38, and distal segment 137 of balloon catheter 130 is pushed through opening 56 in lateral nasal wall 44. The balloon 134 is inflated to 9 bars for 20 seconds then deflated. Deflated balloon 134 is slightly repositioned to assure total dilation of the opening 56. A second dilation of the balloon 134 to a pressure of 9 bars for 20 seconds is performed. The balloon catheter 130 is then deflated and withdrawn from opening 56 and nasal cavity 38.

Figure 10:
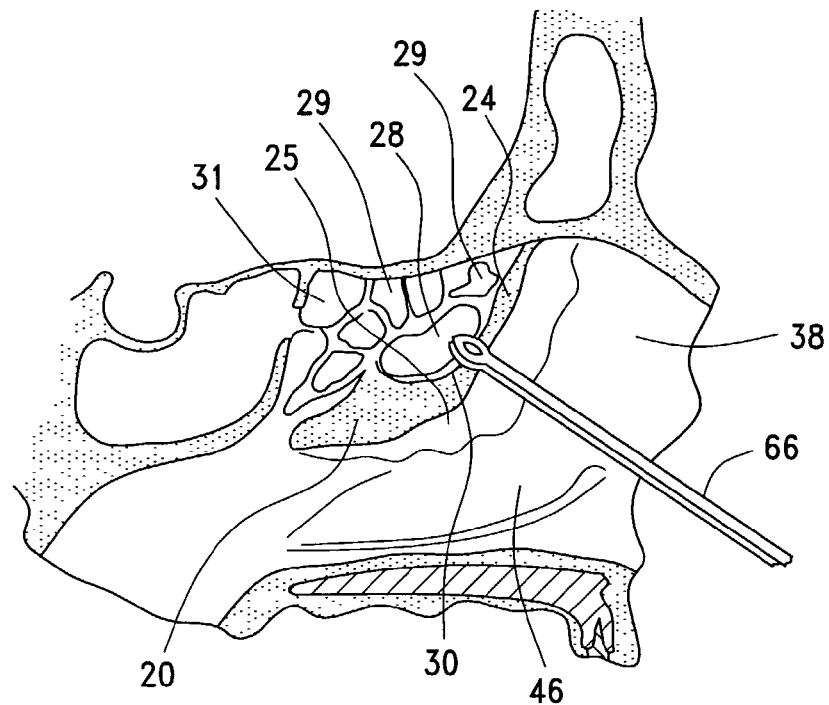
FIG. 10 is a schematic view of a fourth method of the invention showing the cutting forceps making a new opening in the anterior wall of the ethmoid bulla.
Figure 11:
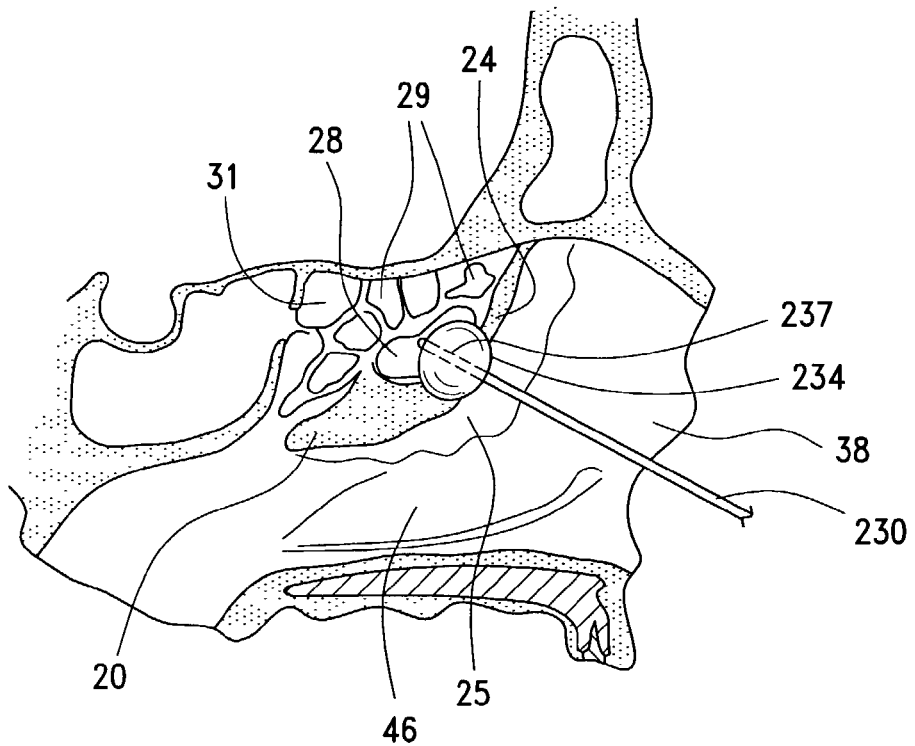
FIG. 11 is a schematic view of another step of the method of FIG. 10 showing the straight sinus balloon catheter dilating the ethmoid bulla.
Figure 12:
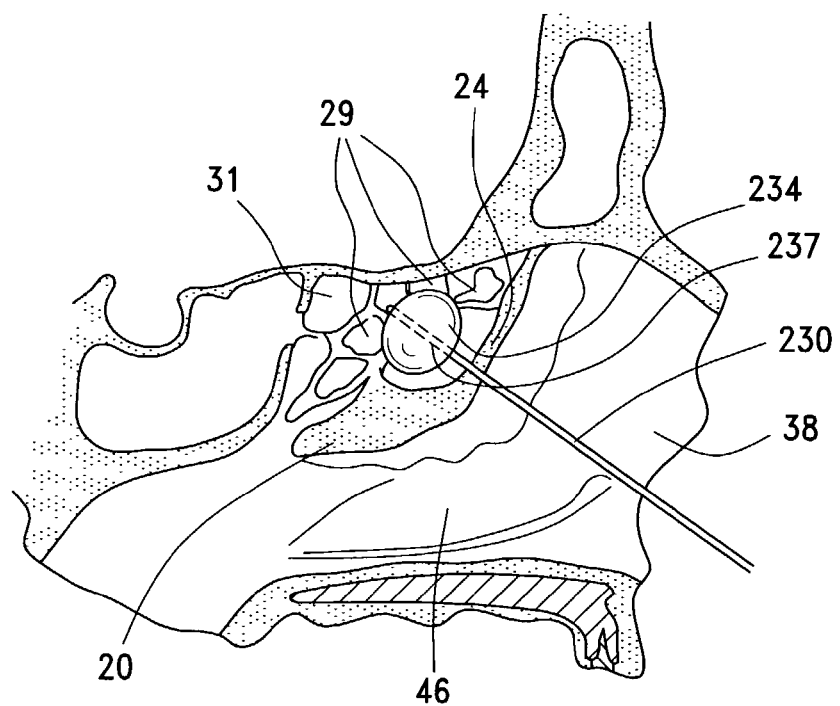
FIG. 12 is a schematic view of yet another step of the method of FIG. 10 showing the straight sinus balloon catheter dilating the ethmoid air cells and thus completing the anterior ethmoidectomy.

A balloon catheter ethmoidectomy of the anterior ethmoid sinus is shown in FIGS. 10-12. The middle turbinate 20 (FIG. 5) has been retracted medially to gain access to the middle meatus 22 (FIG. 5). In some cases, the middle turbinate may be partially or totally removed. The ethmoid infundibulum 24 is exposed by removing part of the uncinate process 26 (FIG. 4). A fine cutting forceps 66 is used to remove the anterior wall 30 of the ethmoid bulla 28 (FIG. 10). After anterior wall 30 of ethmoid bulla 28 is removed, the straight balloon catheter 230 is brought into nasal cavity 38, and distal segment 237 is pushed into bulla 28 (FIG. 11). Balloon 234 is inflated to 9 bars for 20 seconds then deflated. Balloon catheter 230 is then withdrawn from bulla 28. Distal segment 237 of balloon catheter 230 is then pushed into the anterior ethmoid air cells 29 which lie posterior to the previously removed ethmoid bulla 28 (FIG. 12). Balloon 234 is inflated to 9 bars for 20 seconds then deflated. Balloon catheter 230 is then slightly repositioned to insure thorough dilation and inflated again to 9 bars for 20 seconds, deflated, and removed from the area of anterior ethmoid cells 29.

Figure 13:
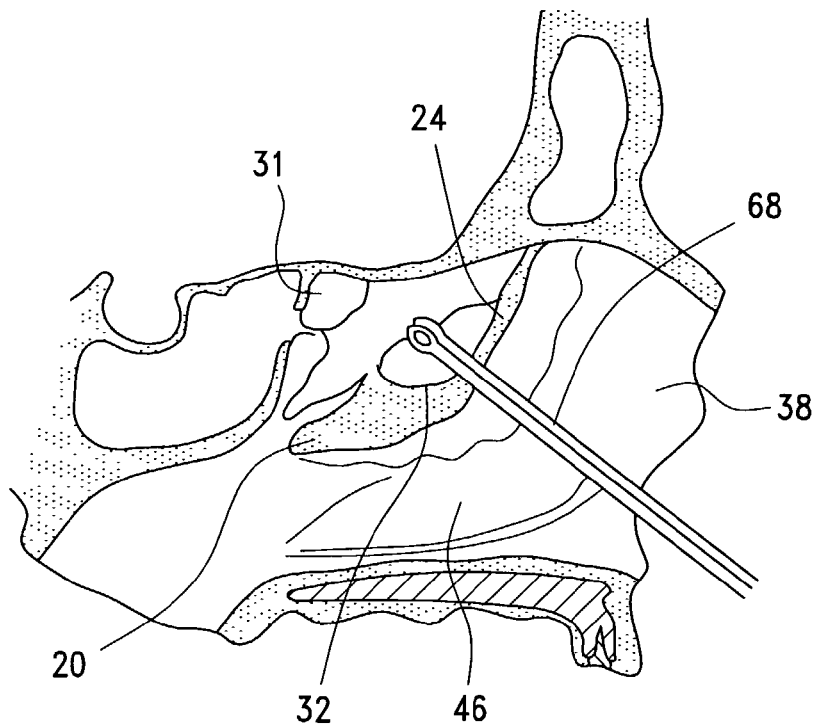
FIG. 13 is a schematic view of yet another step of the method of FIG. 10 showing a punch perforating the basal lamella of the middle turbinate.
Figure 14:
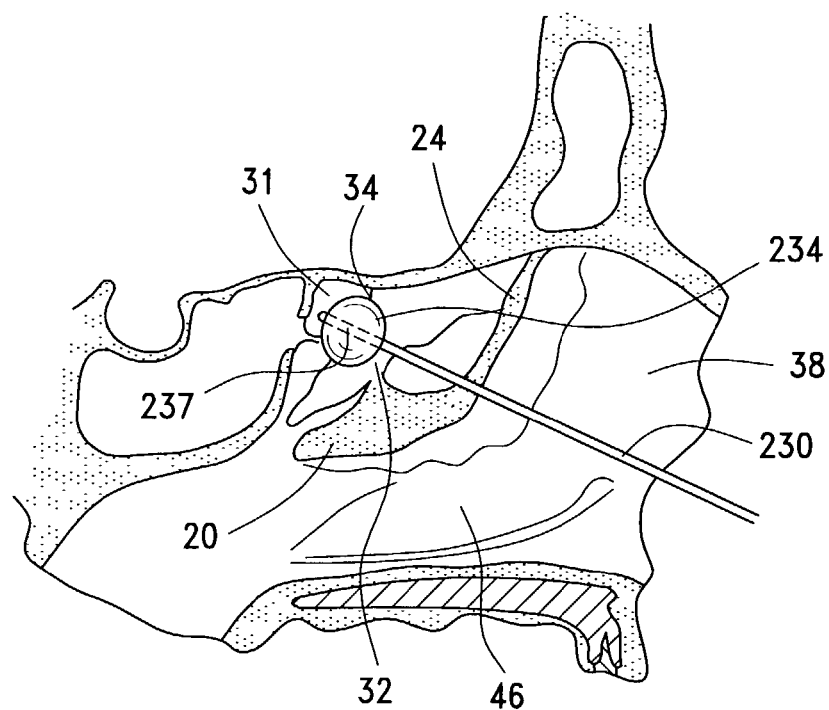
FIG. 14 is a schematic view of still another step of the method of FIG. 10 showing the straight sinus balloon catheter dilating the posterior ethmoid air cells and thus completing the posterior ethmoidectomy.

FIGS. 13 and 14 illustrate an ethmoidectomy of the posterior ethmoid sinus. When the posterior ethmoid sinus cells 31 must be removed, the basal lamella 32 of the middle turbinate 20 is perforated with a punch 68 (FIG. 13). Distal segment 237 of balloon catheter 230 is then pushed through the new opening 34 in the basal lamella 32 of the middle turbinate 20 into the posterior ethmoid air cells 31 and inflated 9 bars for 20 seconds (FIG. 14). Balloon catheter 230 is then deflated, slightly repositioned, and again inflated 9 bars for 20 seconds. Balloon catheter 230 is then deflated and withdrawn.

Figure 15:
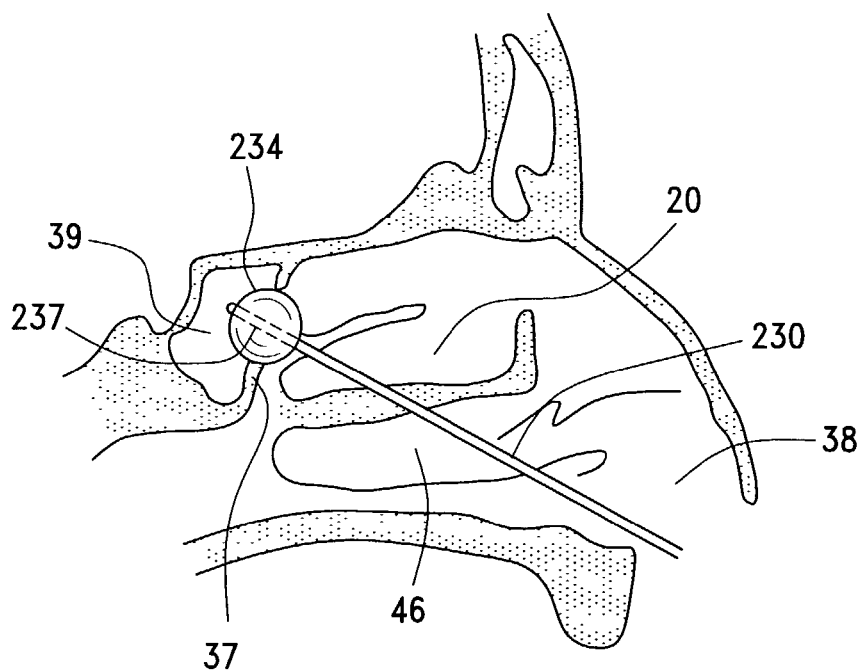
FIG. 15 is a schematic view of an additional step of the method of FIG. 10 showing the sinus balloon catheter dilating the anterior wall of the sphenoid sinus.

FIG. 15 shows sinusotomy of the sphenoid sinus. After anterior and posterior ethmoidectomy, distal segment 237 of balloon catheter 230 is inserted through the anterior wall 37 of sphenoid sinus 39 (FIG. 15). The balloon 234 is then inflated to 9 bars for 20 seconds then deflated. The balloon catheter 230 is slightly repositioned to insure thorough dilation and inflated again to 9 bars for 20 seconds, then deflated, and withdrawn.

Figure 16:
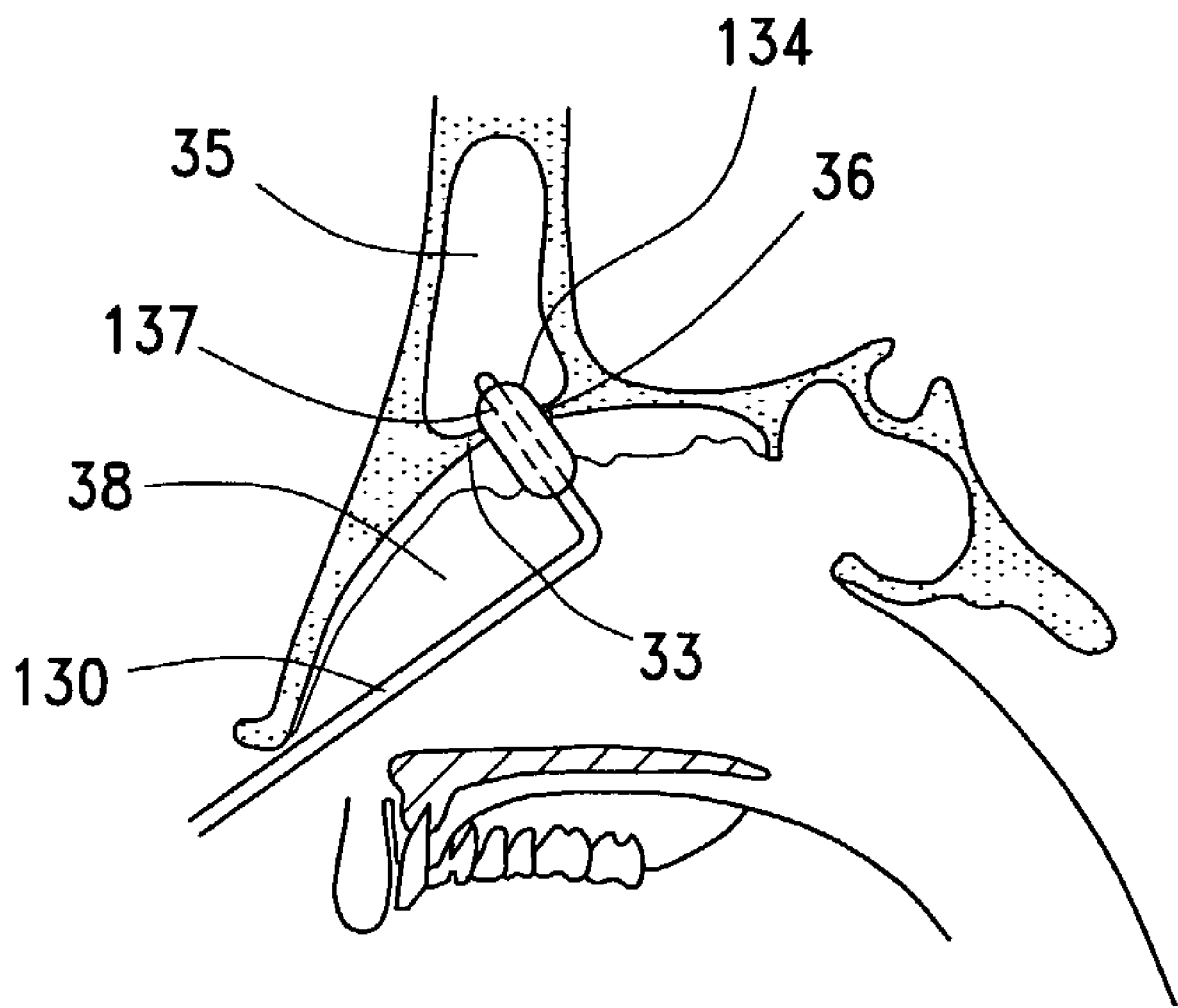
FIG. 16 if a schematic view of a further step of the method of FIG. 10 showing the angled sinus balloon catheter dilating the frontonasal duct.

FIG. 16 illustrates sinusotomy of the frontal sinus. After an anterior ethmoidectomy the nasofrontal duct 36 is exposed and in the surgeon's view. The distal segment 137 of an angled catheter 130 with a 5 mm inflated working diameter is brought into the frontnasal duct 36 and inflated to 9 bars, then deflated. The distal segment 137 of the balloon catheter 130 is slightly repositioned to insure complete dilation of the nasofrontal duct 36 and inflated to 9 bars for 20 seconds then deflated and withdrawn.

All of the above procedures may be performed in a similar fashion in patients who have had previous sinus surgery and the sinus openings have been obstructed by scar tissue or granulation tissue.

The invention claimed is:

1. A device for dilating a surgically prepared small, tight opening in a paranasal sinus, an obstructed or narrowed bony duct, opening or ostium between the paranasal sinus and nasal cavity, said device comprising:
   a tubular body having a proximal end, a proximal segment, a distal end, and a distal segment;
   an inflatable member proximate to said distal segment;
   said inflatable member being capable of dilating a surgically prepared small, tight opening in a paranasal sinus, an obstructed or narrowed bony duct, opening or ostium between the paranasal sinus and nasal cavity;
   wherein said distal segment is at a preset angle of less than 180 degrees to said proximal segment; wherein said tubular body is dimensioned and has sufficient stiffness and column strength to enable said inflatable member, when said inflatable member is deflated, to be inserted transnasally through a nasal cavity and pushed, without being supported and guided by a guide wire, snugly into a surgically prepared small, tight opening in a paranasal sinus, an obstructed or narrowed bony duct, opening or ostium between the paranasal sinus and nasal cavity.

2. The device of claim 1, wherein said angle is between approximately 70 degrees and approximately 150 degrees.

3. The device of claim 1, wherein said angle is between approximately 70 degrees and approximately 115 degrees.

4. The device of claim 1, wherein said angle is between approximately 130 degrees and approximately 150 degrees.

5. The device of claim 1, wherein said angle is approximately 90 degrees.

6. The device of claim 1, wherein said inflatable member has a length between approximately 4 millimeters and approximately 30 millimeters.

7. The device of claim 1, wherein said inflatable member has a working inflated diameter between approximately 2 millimeters and approximately 14 millimeters.

8. The device of claim 1, wherein said distal segment is dimensioned to allow it to be rotated within said nasal cavity.

9. The device of claim 1, wherein said body has a rounded bend between said proximal segment and said distal segment.

10. The device of claim 1, wherein said inflatable member comprises a distal neck and a proximal neck wherein said proximal neck is bonded to said distal segment.

11. The device of claim 10, wherein said inflatable member further comprises a working segment located entirely distal to said bend.

12. The device of claim 1, wherein said body has a length between approximately 4 inches and approximately 10 inches.

13. The device of claim 1, wherein said body has a length of approximately 6 inches.

14. The device of claim 1, wherein said device further comprises a luer attached to said proximal end.

15. The device of claim 14, wherein said luer has means for improving a user's grip on said device while said inflatable member is being inserted.

16. A device for dilating a surgically prepared small, tight opening in a paranasal sinus, an obstructed or narrowed bony duct, opening or ostium between the paranasal sinus and nasal cavity, said device comprising:
  a tubular body having a proximal end, a proximal segment, a distal end, and a distal segment;
  an inflatable member proximate to said distal segment;
  said inflatable member being capable of dilating a surgically prepared small, tight opening in a paranasal sinus, an obstructed or narrowed bony duct, opening or ostium between the paranasal sinus and nasal cavity;
  wherein said distal segment is at a preset angle of less than 180 degrees to said proximal segment;
  wherein said tubular body is dimensioned and has sufficient stiffness and column strength, in absence of a rigidizing member or guide wire, to enable said inflatable member, when said inflatable member is deflated, to be inserted transnasally through a nasal cavity and pushed snugly into a surgically prepared small, tight opening in a paranasal sinus, an obstructed or narrowed bony duct, opening or ostium between the paranasal sinus and nasal cavity.

17. The device of claim 16, which further comprises said tubular body having sufficient stiffness and column strength to enable said inflatable member to be directably pushed while substantially maintaining said angle into a surgically prepared small, tight opening in a paranasal sinus, an obstructed or narrowed bony duct, opening or ostium between the paranasal sinus and nasal cavity.

18. The device of claim 16, which further comprises said tubular body having sufficient stiffness and column strength to enable said inflatable member to be pushed, rotated and translated while substantially maintaining said angle into a surgically prepared small, tight opening in a paranasal sinus, an obstructed or narrowed bony duct, opening or ostium between the paranasal sinus and nasal cavity.

19. The device of claim 16, wherein said angle is between approximately 70 degrees and approximately 150 degrees.

20. The device of claim 16, wherein said angle is between approximately 70 degrees and approximately 115 degrees.

* * * * *